US008987516B2

(12) United States Patent
Umemoto

(10) Patent No.: US 8,987,516 B2
(45) Date of Patent: Mar. 24, 2015

(54) PROCESS FOR PRODUCING ARYLSULFUR PENTAFLUORIDES

(75) Inventor: Teruo Umemoto, Westminster, CO (US)

(73) Assignee: UBE Industries, Ltd., Tokyo (JP)

( * ) Notice: Subject to any disclaimer, the term of this patent is extended or adjusted under 35 U.S.C. 154(b) by 914 days.

(21) Appl. No.: 12/882,469

(22) Filed: Sep. 15, 2010

(65) Prior Publication Data

US 2011/0004022 A1    Jan. 6, 2011

Related U.S. Application Data

(62) Division of application No. 12/473,129, filed on May 27, 2009, now Pat. No. 7,851,646, which is a division of application No. 12/053,775, filed on Mar. 24, 2008, now Pat. No. 7,592,491.

(60) Provisional application No. 60/896,669, filed on Mar. 23, 2007.

(51) Int. Cl.
*C07C 381/00* (2006.01)
*C07C 209/74* (2006.01)

(52) U.S. Cl.
CPC .................................... *C07C 381/00* (2013.01)
USPC ........................................... 564/412; 568/74

(58) Field of Classification Search
CPC ............................ C07C 209/74; C07C 381/00
USPC ............................................ 568/74; 564/412
See application file for complete search history.

(56) References Cited

U.S. PATENT DOCUMENTS

| | | | |
|---|---|---|---|
| 3,054,661 A | 9/1962 | Muetterties | |
| 3,919,204 A | 11/1975 | Boswell, Jr. et al. | |
| 4,147,733 A | 4/1979 | Fiske et al. | |
| 4,316,906 A | 2/1982 | Ondetti et al. | |
| 5,055,223 A | 10/1991 | Reiffenrath et al. | |
| 5,093,432 A | 3/1992 | Bierschenk et al. | |
| 5,395,916 A | 3/1995 | Mochizuki et al. | |
| 5,455,373 A | 10/1995 | Kawa | |
| 5,691,081 A | 11/1997 | Krause et al. | |
| 5,741,935 A | 4/1998 | Bowden et al. | |
| 5,789,580 A | 8/1998 | Chambers et al. | |
| 5,824,827 A | 10/1998 | Bildinov et al. | |
| 6,222,064 B1 | 4/2001 | Lal et al. | |
| 6,737,193 B2 | 5/2004 | Umemoto | |
| 6,958,415 B2 | 10/2005 | Lal et al. | |
| 7,015,176 B2 * | 3/2006 | Bailey et al. | 562/527 |
| 7,045,360 B2 | 5/2006 | Shair et al. | |
| 7,087,681 B2 | 8/2006 | Umemoto | |
| 7,265,247 B1 | 9/2007 | Umemoto et al. | |
| 7,279,584 B2 | 10/2007 | Tomisawa et al. | |
| 7,351,863 B2 | 4/2008 | Hara et al. | |
| 7,381,846 B2 | 6/2008 | Umemoto et al. | |
| 7,501,543 B2 | 3/2009 | Umemoto et al. | |
| 7,592,491 B2 | 9/2009 | Umemoto | |
| 7,820,864 B2 | 10/2010 | Umemoto et al. | |
| 7,851,646 B2 | 12/2010 | Umemoto | |
| 7,919,635 B2 | 4/2011 | Umemoto | |
| 8,030,516 B2 | 10/2011 | Umemoto et al. | |
| 8,203,003 B2 | 6/2012 | Umemoto et al. | |
| 2001/0021792 A1 | 9/2001 | Nakada et al. | |
| 2001/0049457 A1 | 12/2001 | Stephens | |
| 2003/0060669 A1 | 3/2003 | Shibata et al. | |
| 2004/0022720 A1 | 2/2004 | Low et al. | |
| 2004/0106827 A1 | 6/2004 | Dolbier et al. | |
| 2004/0209854 A1 | 10/2004 | Barkalow et al. | |
| 2004/0249209 A1 | 12/2004 | Bailey, III et al. | |
| 2005/0012072 A1 | 1/2005 | Bailey, III et al. | |
| 2005/0148652 A1 | 7/2005 | Kleemann et al. | |
| 2006/0014972 A1 | 1/2006 | Hara et al. | |
| 2009/0105502 A1 | 4/2009 | Umemoto et al. | |
| 2009/0203924 A1 | 8/2009 | Umemoto et al. | |
| 2009/0287024 A1 | 11/2009 | Umemoto et al. | |
| 2010/0029992 A1 | 2/2010 | Umemoto et al. | |
| 2010/0076215 A9 | 3/2010 | Umemoto et al. | |
| 2010/0152463 A1 | 6/2010 | Umemoto et al. | |
| 2010/0174096 A1 | 7/2010 | Umemoto et al. | |
| 2010/0234605 A1 | 9/2010 | Umemoto et al. | |
| 2011/0009672 A1 | 1/2011 | Umemoto | |
| 2011/0160488 A1 | 6/2011 | Umemoto | |
| 2011/0166392 A1 | 7/2011 | Umemoto | |
| 2011/0190511 A1 | 8/2011 | Umemoto et al. | |
| 2011/0275833 A1 | 11/2011 | Umemoto et al. | |

(Continued)

FOREIGN PATENT DOCUMENTS

DE    19748109 A1    5/1999
EP    0361907 A2    4/1990

(Continued)

OTHER PUBLICATIONS

Ou, X., Bernard, G.M., Janzen, A.F. "Oxidative addition and isomerization reactions. The synthesis of cis- and trans- ArSF4Cl and cis- and trans-PhTeF4Cl" Canadian Journal of Chemistry, 75, (1997), p. 1878-1884.*
Darraugh "Chlorofluorination Reactions of Sulphur(IV) Fluorides" J. Chem. Soc. Chem. Commun. 1969, p. 864-865.*
Umemoto et al (2010) "Discovery of 4-tert-Butyl-2,6-dimethylphenylsulfur Trifluoride as a Deoxofluorinating Agent with High Thermal Stability as Well as Unusual Resistance to Aqueous Hydrolysis, and Its Diverse Fluorination Capabilities Including Deoxofluoro-Arylsulfinylation with High Stereoselectivity" JACS 132:18199-18205.
Davis et al (1999) "Efficient Asymmetric Synthesis of β-Fluoro α-Amino Acids" J. Org. Chem. 64:6931-6934.
Hu and DesMarteau (1993) "Synthesis of Perhaloalkanesulfonyl Halides and Their Sulfonimide Derivatives" Inorg. Chem. 32:5007-5010.

(Continued)

*Primary Examiner* — Jafar Parsa
*Assistant Examiner* — Amy C Bonaparte
(74) *Attorney, Agent, or Firm* — Swanson & Bratschun, L.L.C.

(57) ABSTRACT

Novel processes for preparing arylsulfur pentafluorides are disclosed. Processes include reacting at least one aryl sulfur compound with a halogen and a fluoro salt to form an arylsulfur halotetrafluoride. The arylsulfur halotetrafluoride is reacted with a fluoride source to form a target arylsulfur pentafluoride.

8 Claims, No Drawings

(56) References Cited

U.S. PATENT DOCUMENTS

| | | |
|---|---|---|
| 2011/0301382 A1 | 12/2011 | Umemoto et al. |
| 2011/0306798 A1 | 12/2011 | Umemoto |
| 2012/0157716 A1 | 6/2012 | Umemoto et al. |

FOREIGN PATENT DOCUMENTS

| | | |
|---|---|---|
| EP | 1484318 A1 | 12/2004 |
| GB | 2276379 | 9/1994 |
| JP | H02-154266 A | 6/1990 |
| JP | 2003-077861 | 4/1991 |
| JP | H07-292050 A | 11/1995 |
| JP | H09-500893 A | 1/1997 |
| JP | 2000-38370 A | 8/2000 |
| JP | 2004-359687 A | 12/2004 |
| JP | 4531852 | 6/2010 |
| TW | 270111 | 2/1996 |
| TW | I 325857 | 6/2010 |
| TW | I 327135 | 7/2010 |
| WO | WO 94/21606 | 9/1994 |
| WO | WO 01/27076 | 4/2001 |
| WO | WO 03/002553 | 1/2003 |
| WO | WO 2004/011422 | 2/2004 |
| WO | WO 2004/050676 | 6/2004 |
| WO | WO 2008/013550 | 1/2008 |
| WO | WO 2008/014345 | 1/2008 |
| WO | WO 2008/118787 | 10/2008 |
| WO | WO 2009/076345 | 6/2009 |
| WO | WO 2009/114409 | 9/2009 |
| WO | WO 2010/014665 | 2/2010 |
| WO | WO 2010/022001 | 2/2010 |
| WO | WO 2010/033930 | 3/2010 |
| WO | WO 2010/081014 | 7/2010 |

OTHER PUBLICATIONS

Huang and Lu (1992) "The Reaction of Perfluoroalkanesylfonyl Halides" Chinese Journal of Chemistry Chapter VII 10(3):268-273.
Huang and Lu (1992) "The Reaction of Perfluoroalkanesylfonyl Halides" Chinese Journal of Chemistry Chapter VIII 10(3):274-277.
Notice of Allowance mailed Jul. 26, 2011 with respect to U.S. Appl. No. 12/253,030.
Notice of Allowance mailed Jun. 21, 2011 with respect to U.S. Appl. No. 12/253,030.
Notice of Allowance mailed Dec. 7, 2010 with respect to U.S. Appl. No. 12/367,171.
Office Action mailed Aug. 4, 2011 with respect to U.S. Appl. No. 12/647,973.
Office Action mailed Jun. 1, 2011 with respect to U.S. Appl. No. 12/633,414.
Office Action mailed Jan. 21, 2011 with respect to U.S. Appl. No. 12/305,868.
Office Action mailed Sep. 13, 2010 with respect to U.S. Appl. No. 12/633,414.
Office Action mailed Mar. 2, 2010 with respect to U.S. Appl. No. 12/473,129.
Oae, Shigeru (1977) "Sulfoxides and Sulfilimines" Organic Chemistry of Sulfur, Plenum Press, NY and London, Chapters 8 and 10, pp. 384-589.
Oae, Shigeru (1977) "Sulfoxides and Sulfilimines" Organic Chemistry of Sulfur, Plenum Press, NY and London, Chapter 10, Section 10.3.7, pp. 572-577.
Patai and Rappoport (1994) "Synthesis of Sulphoxides" The Synthesis of Sulphones, Sulphoxides and Cyclic Sulphides, John Wiley & Sons, an Interscience Publication, Chapter 3, pp. 109-158.
Sheppard (1973) "Phenylsulfur Tri Fluoride" Organic Syntheses, Coll. 5:959; (1964) 44:82.
Whitham, Gordon H. (1995) "Organosulfur Chemistry" Oxford Chemistry Primers, 33, Oxford Science Publications, Chapter 3, pp. 34-63 (ISBN-13: 9780198558996).
Andrieux et al. (1990) "Outer-sphere and inner-sphere processes in organic chemistry. Reaction of trifluoromethyl bromide with electrochemically generated aromatic anion radicals and sulfur dioxide anion radicals" J. Am. Chem. Soc. 112(2): 786-791.
Bégué and Bonnet-Delpon (2006) "Recent Advances (1995-2005) in Fluorinated Pharmaceuticals Based on Natural Products" Journal of Fluorine Chemistry 127:992-1012+A3.
Bowden et al. (2000) "A New Method for the Synthesis of Aromatic Sulfurpentafluorides and Studies of the Stability of the Sulfurpentafluoride Group in Common Synthetic Transformation" Tetrahedron 56:3399-3408.
Bunnelle et al. (1990) "Difluorination of Esters. Preparation of α, α-Difluoro Ethers" J. Org. Chem. 55(2):768-770.
Calamari and Trask (1979) "Laboratory Explosions" Chemical & Engineering News, 57(19):4.
Cava and Levinson (1985) "Thionation Reactions of Lawesson's Reagents" Tetrahedron 41(22):5061-5087.
Chambers et al. (1996) "Elemental Fluorine. Part 5.1,2 Reactions of 1,3-Dithiolanes and Thioglycosides With Fluorine-Iodine Mixtures" J. Chem. Soc. Perkin Trans. 1 1941-1944.
Cochran (Mar. 19, 1979) "Laboratory Explosions" Chemical & Engineering News 57(19):4.
Des Marteau (1995) "Novel perfluorinated ionomers and ionenes" J. Fluorine Chem. 72(2): 203-208.
Feiring (1979) "Chemistry in Hydrogen Fluoride. 7. A Novel Synthesis of Aryl Trifluoromethyl Ethers" J. Org. Chem. 44(16):2907-2910.
Folest et al. (1988) "Electrochemical Synthesis of Trifluoromethane Sulfinic Acid Salt From CF3Br and SO2" Synthetic Communications 18(13): 1491-1494.
Furuya et al. (2005) "Synthesis of gem-difluorides From Aldehydes Using DFMBA" Journal of Fluorine Chemistry 126:721-725.
Hasek et al. (1960) "The Chemistry of Sulfur Tetrafluoride. II. The Fluorination of Organic Carbonyl Compounds" Journal of American Chem. Soc. 82(3):543-551.
Hayashi et al. (2002) "2,2-Difluoro-1,3-dimethylimidazolidine (DFI). A New Fluorinating Agent" Chem. Commun. 1618-1619.
Henne and Nager (1951) "Trifluoropropyne" J. Am. Chem. Soc. 73(3):1042-1043.
Hollitzer and Sartori (1987) "The electrochemical perfluorination (ECPF) of propanesulfonyl fluorides. I: Preparation and ECPF of 1-propanesulfonyl fluoride and 1,3-propanedisulfonyl difluoride" J. Fluorine Chem. 35(2): 329-341.
Hoover and Coffman (1964) "Synthesis and Chemistry of Ethynylsulfur Pentafluoride" Journal of Organic Chem. 29:3567-3570.
Howe-Grant (1995) "Sulfur Hexafluoride" Fluorine Chemistry: A Comprehensive Treatment, John Wiley & Sons, Inc., New York (ISBN: 0-471-12031-6) pp. 188-195.
Huang and Guo (1981) "The Reaction of Arylsulfur Trifluoride With Sterols" Shanghai Institute of Organic Chemistry, ACTA Chimica Sinica 39(1):68.
Kirsch and Bremer (2000) "Nematic Liquid Crystals for Active Matrix Displays: Molecular Design and Synthesis" Angew. Chem. Int. Ed. 39:4216-4235.
Kirsch and Hahn (2005) "Liquid Crystals Based on Hypervalent Sulfur Fluorides: Exploring the Steric Effects of ortho-Fluorine Substituents" Eur. J. of Org. Chem. 3095-3100.
Kobayashi et al.(2004) "Deoxyfluorination of alcohols using N,N-diethyl-α, α-difluoro-(m-methylbenzyl)amine" Tetrahedron 60:6923-6930.
Kuroboshi et al. (1992) "Oxidative Desulfurization-Fluorination of Xanthates. A Convenient Synthesis of Trifluoromethyl Ethers and Difluoro(methylthio)methyl Ethers" Tetrahedron 33(29): 4173-4176.
Kuroboshi and Hiyama (1991) "A Facile Synthesis of Difluoromethylene Compounds by Oxidative Fluorodesulfurization of Dithioacetals Using Tetrabutylammonium Dihydrogentrifluoride and N-Halo Compounds" Synlett 909-910.
Kuroboshi and Hiyama (1992) "A Facile Synthesis of Trifluoromethylamines by Oxidative Desulfurization-Fluorination of Dithiocarbamates" Tetrahedron 33(29):4177-4178.

(56) References Cited

OTHER PUBLICATIONS

Kuroboshi and Hiyama (1992) "Oxidative Desulfurization-Fluorination of Methyl Arenedithiocarboxylates. A Convenient Synthesis of Trifluoromethylated Aromatic Compounds" Chemistry Letters 827-830.

Kuroboshi and Hiyama (1994) "A Convenient Synthesis of Perfluoroalkylated Amines by Oxidative Desulfurization-Fluorination" Tetrahedron 35(23):3983-3984.

Kuroboshi and Hiyama (1994) "A Facile Synthesis of α, α-Difluoroalkyl Ethers and Carbonyl Fluoride Acetals by Oxidative Desulfurization-Fluorination" Synlett 251-252.

Lal et al. (1999) "Bis(2-methoxyethyl)aminosulfur trifluoride: a new broad-spectrum deoxofluorinating agent with enhanced thermal stability" Chem. Commun.215-216.

Lal et al. (2000) "Fluorination of Thiocarbonyl Compounds with Bis(2-methoxyethyl)aminosulfur Trifluoride (Deoxo-Fluor Reagent): A Facile Synthesis of gem-Difluorides" J. Org. Chem. 65:4830-4832.

Lee et al. (1989) "One Pot Phase Transfer Synthesis of O-Alkyl, S-Methyl Dithiocarbonates (Xanthates)" Synthetic Communications 19(3&4):547-552.

Ma and Cahard (2007) "Strategies for Nucleophilic, Electrophilic, and Radical Trifluoromethylations" Journal of Fluorine Chemistry 128:975-996.

Mayer and Scheithauer (1985) Carbonsäuren und Carbonsäure-Derivate E5:891-916.

Methods of Organic Chemistry (Houben-Weyl), Work Bench Edition vol. E 10A, Organo-Fluorine Compounds, Gorge Thieme Verlag Stuttgart, New York, 2000 p.p. 194-201.

Middleton (1975) "New Fluorinating Reagents. Dialkylaminosulfur Fluorides" Journal of Organic Chem. 40(5):574-578.

Moss et al. (1995) "Glossary of Class Names of Organic Compounds and Reactive Intermediates Based on Structure" Pure & Appl. Chem, 67(8/9):1307-1375.

Motherwell and Wilkinson (1991) "Observations on the Reaction of Dithioketals with Para-Iodotoluene Difluoride: A Novel Route to Gem-Difluoro Compounds" Synlett 191-192.

Notice of Allowance mailed Oct. 28, 2010 with respect to U.S. Appl. No. 12/367,171.

Notice of Allowance mailed Jun. 23, 2010 with respect to U.S. Appl. No. 12/473,109.

Notice of Allowance mailed Aug. 6, 2010 with respect to U.S. Appl. No. 12/473,129.

Notice of Allowance mailed Oct. 31, 2008 with respect to U.S. Appl. No. 12/106,460.

Notice of Allowance mailed Apr. 29, 2009 with respect to U.S. Appl. No. 12/053,775.

Office Action mailed Jan. 7, 2010 with respect to U.S. Appl. No. 12/473,109.

Office Action mailed Oct. 22, 2009 with respect to U.S. Appl. No. 12/367,171.

Office Action mailed Nov. 20, 2007 with respect to U.S. Patent No. 7,381,846.

Office Action mailed Dec. 3, 2008 with respect to U.S. Patent No. 7,592,491.

Olah et al. (1974) "Synthetic Methods and Reactions. I. Selenium Tetrafluoride and Its Pyridine Complex. Convenient Fluorinating Agents for Fluorination of Ketones, Aldehydes, Amides, Alcohols, Carboxylic Acids, and Anhydrides" Journal of American Chem. Soc. 96(3):925-927.

Ou et al. (1997) "Oxidative Addition and Isomerization Reactions. The Synthesis of cis-and trans- ArSF4Cl and cis- and trans-PHTeF4C1" Can. Journal of Chem. 75:1878-1884.

Ou and Janzen (2000) "Oxidative Fluorination of S, Se and Te Compounds" Journal of Fluorine Chem. 101:279-283.

Pashinnik et al. (2003) "A New Method for the Synthesis of Organosulfur Trifluorides" Synthetic Communications 33(14):2505-2509.

Petrov et al. (2001) "1,1,2,2-Tetrafluoroethyl-N,N-dimethylamine: A New Selective Fluorinating Agent" Journal of Fluorine Chemistry 109:25-31.

Petrov et al. (2004) "Quadricyclane—thermal cycloaddition to polyfluorinated carbonyl compounds: A simple synthesis of polyfluorinated 3-oxatricyclo[4.2.1.02,5]non-7-enes" Journal of Fluorine Chem. 125(10): 1543-1552.

Prakash et al. (1993) "Simplified Preparation of α, α-Difluorodiphenlmethanes From Benzophenone 1,3-Dithiolanes With Sulfuryl Choride and Pyridinium Polyhydrogen Fluoride" Synlett 691-693.

Qiu and Burton (1993) "A useful synthesis of ω-iodoperfluoroalkanesulfonyl fluorides and perfluoroalkane-α,ω-bis-sulfonyl fluorides" J. Fluorine Chem. 60(1): 93-100.

Reddy et al. (2005) "gem-Difluorination of 2,2-Diaryl-1,3-dithiolanes by Selectfluor® and Pyridinium Polyhydrogen Fluoride" Chem. Commun. 654-656.

Rozen and Mishani (1993) "Conversion of Esters to α, α-Difluoro Ethers Using Bromine Trifluoride" J. Chem. Soc. Commun. 1761-1762.

Sasson et al. (2003) "Novel Method for Incorporating the CHF2 Group into Organic Molecules Using BrF3" Organic Letters 5(5):769-771.

Scheeren et al. (1973) "A General Procedure for the Conversion of a Carbonyl Group into a Thione Group with Tetraphosphorus Decasulfide" Communications 149-151.

Seergeva and Dolbier (2004) "A New Synthesis of Pentafluorosulfanylbenzene" Organic Letters 6(14):2417-2419.

Sharts and Sheppard (1974) "Modern Methods to Prepare Monofluoroaliphatic Compounds" Organic Chemistry 21:158-173.

Sheppard (1962) "Arylsulfur Pentafluorides" J. Am. Chem. Soc. 84:3064-3072.

Sheppard (1962) "Alkyl- and Arylsulfur Trifluorides" J. Chem. Soc. 84:3058-3063.

Sheppard and Foster (1972) "Pentafluorophenylsulfur(IV) Derivatives" Journal of Fluorine Chemistry 2:53-61.

Sheppard and Taft (1972) "The Electronic Properties of Di-, Tri-, Tetra-, and Hexacoordinate Sulfur Substituents" Journal Am. Chem. Soc. 94(6)1919-1923.

Shimizu et al. (1995) "Gem-Difluorination of 1,3-Dithiolanes with the Hexafluoropropene-Diethylamine reagent and N-Iodosuccinimide or 1,3-Dibromo-5,5-Dimethylhydantoin" Journal of Fluorine Chemistry 71:9-12.

Simons and Lewis (1938) "The Preparation of Benzotrifluoride" J. Am. Chem. Soc. 60(2):492.

Sipyagin et al. (2001) "Preparation of the First Ortho-Substituted Pentafluorosulfanylbenzenes" Journal of Fluorine Chemistry 112:287-295.

Smith et al. (1960) "Chemistry of Sulfur Tetrafluoride. III. Organoiminosulfur Difluorides" Journal of American Chem. Soc. 82(3):551-555.

Sondej and Katzenellenbogen (1986) "Gem-Difluoro Compounds: A Convenient Preparation from Ketones and Aldehydes by Halogen Fluoride Treatment of 1,3-Dithiolanes" J. Org. Chem. 51:3508-3513.

Tarrant et al. (1954) "Fluoroölefins. V. The Synthesis of 1,1-Difluoro-3-Methylbutadiene" J. Am. Chem. Soc. 76(9): 2343-2345.

Thayer (2006) "Fabulous Fluorine" Chemical & Engineering News 84(23):15-24.

Thayer (2006) "Constructing Life Sciences Compounds" Chemical & Engineering News 84(23):27-32.

Tordeux et al. (1990) "Reactions of trifluoromethyl bromide and related halides: part 9. Comparison between additions to carbonyl compounds, enamines, and sulphur dioxide in the presence of zinc" J. Chem. Soc., Perkin Trans. 1 1951-1957.

Tozer and Herpin (1996) "Methods for the Synthesis of gem-Difluoromethylene Compounds" Tetrahedron 52(26): 8619-8683.

Tullock (1960) "The Chemistry of Sulfur Tetrafluoride. I. The Synthesis of Sulfur Tetrafluoride" Journal of American Chem. Soc. 82(3):539-542.

Uneyama (2006) "Nucleophilic Substitution on Fluoroaromatic Rings" Organofluorine Chemistry, Blackwell Publishing Ltd., Oxford, UK (ISBN-13: 978-14051-2561-1) pp. 101-107.

(56) References Cited

OTHER PUBLICATIONS

Winter and Gard (2004) "Synthesis of SF5-benzene (SF5C6H5) by the SF5-halide Method" Journal of Fluorine Chem. 125:549-552.
Yoshiyama and Fuchigami (1992) "Anodic gem-Difluorination of Dithioacetals" Chemistry Letters 1995-1998.
Xiaobo et al. (1997) "Oxidative Addition and Isomerization Reactions—The Synthesis of cis-ArSF$_4$Cl and trans-ArSF$_4$Cl and cis-PhTeF$_4$Cl and trans-PhTeF$_4$Cl" Canadian Journal of Chemistry, 75(12):1878-1884.
Ariyan and Wiles (1961) Journal of Chemical Society 888:4510-4514 "The Action of Sulphur Monochloride on Aromatic Hydrocarbons".
European Search Report from EP 12153153, dated May 25, 2012, 7 pages.
European Search Report from EP 12153156, dated May 25, 2012, 7 pages.
European Search Report from EP 12153157, dated May 25, 2012, 7 pages.
European Search Report from EP 12153158, dated May 25, 2012, 8 pages.
Tsuchida et al. (1993) Macromolecules 26:4113-4117 "Thermal Polymerization of Diaryl Disulfides to Yield Poly(arylene sulfide)s".
Yamamoto et al. (1991) J. Chem. Soc., Chem. Commun. 8:596-597 "One-pot Synthesis of Poly(thioarylene)s: Predominant Sulphide Bond Formation through Oxidative and Electrophilic Reaction".

* cited by examiner

PROCESS FOR PRODUCING ARYLSULFUR PENTAFLUORIDES

RELATED APPLICATIONS

This application is a divisional of U.S. application Ser. No. 12/473,129 entitled "Process for Producing Arylsulfur Pentafluorides" filed May 27, 2009, which is a divisional of U.S. application Ser. No. 12/053,775 entitled "Process for Producing Arylsulfur Pentafluorides", filed Mar. 24, 2008, now U.S. Pat. No. 7,592,491, issued Sep. 22, 2009, and claims benefit of U.S. Provisional Application Ser. No. 60/896,669 entitled "Process for Producing Arylsulfur Pentafluorides" filed Mar. 23, 2007, each of which is hereby incorporated by reference in their entirety.

TECHNICAL FIELD

The invention relates to methods and compositions useful in the preparation of arylsulfur pentafluorides.

BACKGROUND OF THE INVENTION

Arylsulfur pentafluorides compounds are used to introduce one or more sulfur pentafluoride groups into various commercial organic molecules. In particular, arylsulfur pentafluorides have been shown as useful compounds (as product or intermediate) in the development of liquid crystals, in bioactive chemicals such as fungicides, herbicides, and insecticides, and in other like materials [see Fluorine-containing Synthons (ACS Symposium Series 911), ed by V. A. Soloshonok, American Chemical Society (2005), pp. 108-113]. However, as discussed herein, conventional synthetic methodologies to produce arylsulfur pentafluorides have proven difficult and are a concern within the art.

Generally, arylsulfur pentafluorides are synthesized using one of the following synthetic methods: (1) fluorination of diaryl disulfies or arylsulfur trifluoride with $AgF_2$ [see J. Am. Chem. Soc., Vol. 84 (1962), pp. 3064-3072, and J. Fluorine Chem. Vol. 112 (2001), pp. 287-295]; (2) fluorination of di(nitrophenyl)disulfides, nitrobenzenethiols, or nitrophenylsulfur trifluorides with molecular fluorine ($F_2$) [see Tetrahedron, Vol. 56 (2000), pp. 3399-3408; Eur. J. Org. Chem., Vol. 2005, pp. 3095-3100; and U.S. Pat. No. 5,741,935]; (3) fluorination of diaryl disulfides or arenethiols with $F_2$, $CF_3OF$, or $CF_2(OF)_2$ in the presence or absence of a fluoride source (see US Patent Publication No. 2004/0249209 A1); (4) fluorination of diaryl disulfides with $XeF_2$ [see J. Fluorine Chem., Vol. 101 (2000), pp. 279-283]; (5) reaction of 1,4-bis(acetoxy)-2-cyclohexene with $SF_5Br$ followed by dehydrobromination or hydrolysis and then aromatization reactions [see J. Fluorine Chem., Vol. 125 (2004), pp. 549-552]; (6) reaction of 4,5-dichloro-1-cyclohexene with $SF_5Cl$ followed by dehydrochlorination [see Organic Letters, Vol. 6 (2004), pp. 2417-2419 and PCT WO 2004/011422 A1]; and (7) reaction of $SF_5Cl$ with acetylene, followed by bromination, dehydrobromination, and reduction with zinc, giving pentafluorosulfanylacetylene, which was then reacted with butadiene, followed by an aromatization reaction at very high temperature [see J. Org. Chem., Vol. 29 (1964), pp. 3567-3570].

Each of the above synthetic methods has one or more drawbacks making it either impractical (time or yield), overly expensive, and/or overly dangerous to practice. For example, synthesis methods (1) and (4) provide low yields and require expensive reaction agents, e.g., $AgF_2$ and $XeF_2$. Methods (2) and (3) require the use of $F_2$, $CF_3OF$, or $CF_2(OF)_2$, each of which is toxic, explosive, and corrosive, and products produced using these methods are at a relatively low yield. Note that handling of these gasses is expensive from the standpoint of the gasses production, storage and use. In addition, synthesis methods that require the use of $F_2$, $CF_3OF$, and/or $CF_2(OF)_2$ are limited to the production of deactivated arylsulfur pentafluorides, such as nitrophenylsulfur pentafluorides, due to their extreme reactivity, which leads to side-reactions such as fluorination of the aromatic rings when not deactivated. Methods (5) and (6) also require expensive reactants, e.g., $SF_5Cl$ or $SF_5Br$, and have narrow application because the starting cyclohexene derivatives are limited. Finally, method (7) requires the expensive reactant $SF_5Cl$ and includes many reaction steps to reach the arylsulfur pentafluorides (timely and low yield). Therefore, problems with the production methods for arylsulfur pentafluorides have made it difficult to prepare the material in a safe, cost effective and timely fashion.

Phenylsulfur chlorotetrafluoride, p-methylphenylsulfur chlorotetrafluoride, and p-nitrophenylsulfur chlorotetrafluoride were detected in the reaction of diphenyl disulfide, bis(p-methylphenyl)disulfide, and bis(p-nitrophenyl)disulfide, respectively, with $XeF_2$ in the presence of tetraethylammonium chloride (see Can. J. Chem., Vol. 75, pp. 1878-1884). Chemical structures of the chlorotetrafluoride compounds were assigned by analysis of the NMR data of the reaction mixtures, but these compounds were not isolated. Therefore, the physical properties of the chlorotetrafluorides were unknown. This synthesis method using $XeF_2$ was industrially impractical because $XeF_2$ is overly expensive for large scale production.

The present invention is directed toward overcoming one or more of the problems discussed above.

SUMMARY OF THE INVENTION

The present invention provides novel processes for the production of arylsulfur pentafluoride, as represented by formula (I):

Embodiments of the invention include reacting at least one aryl sulfur compound, having a formula (IIa) or (IIb),

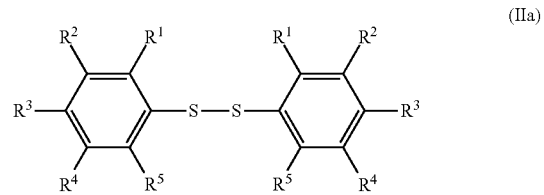

-continued

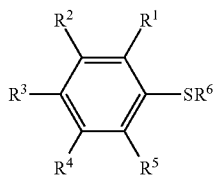
(IIb)

with a halogen selected from the group of chlorine, bromine, iodine and interhalogens, and a fluoro salt ($M^+F^-$, formula III) to form an arylsulfur halotetrafluoride having a formula (IV):

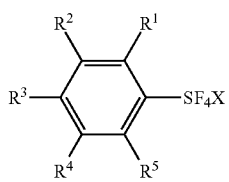
(IV)

The arylsulfur halotetrafluoride (formula IV) is reacted with a fluoride source to form the arylsulfur pentafluoride (formula I).

Embodiments of the present invention also provide processes for producing an arylsulfur pentafluoride (formula I) by reacting at least one aryl sulfur compound, having a formula (IIa) or (IIb), with a halogen selected from the group of chlorine, bromine, iodine and interhalogens, and a fluoro salt ($M^+F^-$, formula III) to form an arylsulfur halotetrafluoride having a formula (IV):

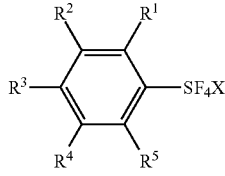
(IV)

The arylsulfur halotetrafluoride (formula IV) is reacted with a fluoride source in the presence of a halogen selected from the group of chlorine, bromine, iodine, and interhalogens to form the arylsulfur pentafluoride (formula I).

Embodiments of the present invention also provide processes for producing arylsulfur pentafluorides (formula I) by reacting an arylsulfur trifluoride having a formula (V):

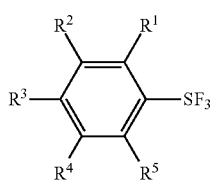
(V)

with a halogen selected from the group of chlorine, bromine, iodine and interhalogens, and a fluoro salt (formula III) to form an arylsulfur halotetrafluoride having a formula (IV):

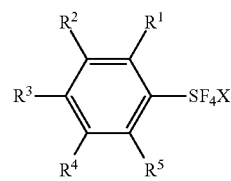
(IV)

The arylsulfur halotetrafluoride (formula IV) is reacted with a fluoride source to form the arylsulfur pentafluoride (formula I).

Embodiments of the present invention also provide processes for producing arylsulfur pentafluorides (formula I) by reacting an arylsulfur trifluoride having a formula (V):

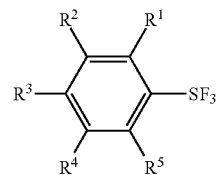
(V)

with a halogen selected from the group of chlorine, bromine, iodine and interhalogens, and a fluoro salt (formula III) to form an arylsulfur halotetrafluoride having a formula (IV).

The arylsulfur halotetrafluoride (formula IV) is reacted with a fluoride source in the presence of a halogen selected from the group of chlorine, bromine, iodine, and interhalogens to form the arylsulfur pentafluoride (formula I).

Embodiments of the present invention further provide processes for producing arylsulfur halotetrafluoride (formula IV) by reacting at least one aryl sulfur compound having a formula (IIa) or (IIb) with a halogen selected from a group of chlorine, bromine, iodine and interhalogens, and a fluoro salt having a formula (III) to form an arylsulfur halotetrafluoride having a formula (IV).

Embodiments of the present invention provide processes for producing an arylsulfur pentafluoride (formula I) by reacting an arylsulfur halotetrafluoride having a formula (IV) with a fluoride source. In some embodiments the fluoride source has a boiling point of approximately 0° C. or more at 1 atm.

Finally, embodiments of the present invention provides processes for producing an arylsulfur pentafluoride (formula I) by reacting an arylsulfur halotetrafluoride having a formula (IV) with a fluoride source in the presence of a halogen selected from the group of chlorine, bromine, iodine, and interhalogens to form the arylsulfur pentafluoride.

In addition, the present invention provides novel arylsulfur chlorotetrafluoride represented by formula (IV') and fluorinated arylsulfur pentafluoride represented by formula (I'):

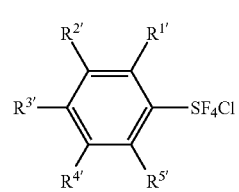
(IV')

-continued

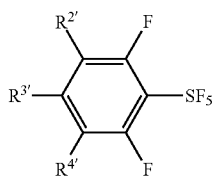

(I')

These and various other features as well as advantages which characterize embodiments of the invention will be apparent from a reading of the following detailed description and a review of the appended claims.

DETAILED DESCRIPTION OF THE INVENTION

Embodiments of the present invention provide industrially useful processes for producing arylsulfur pentafluorides, as represented by formula (I). Prepared arylsulfur pentafluorides can be used, for among other things, to introduce one or more sulfur pentafluoride ($SF_5$) groups into various target organic compounds. Unlike previous methods in the art, the processes of the invention utilize low cost reagents to prepare moderate to excellent yields of arylsulfur pentafluoride compounds. Further, methods of the invention provide a greater degree of overall safety in comparison to most prior art methodologies (for example the use of $F_2$ gas).

A distinction of the present invention is that the processes herein are accomplished at a low cost as compared to other conventional methods. For example, the reagents to perform Xe based reactions are cost prohibitive, whereas the present invention utilizes low cost materials: halogens such as $Cl_2$, $Br_2$, and $I_2$.

Embodiments of the invention include processes which comprise (see for example Scheme 1, Processes I and II) reacting at least one aryl sulfur compound having a formula (IIa) or a formula (IIb) with a halogen selected from the group of chlorine, bromine, iodine, and interhalogens, and a fluoro salt having a formula (III), to form an arylsulfur halotetrafluoride, represented by formula (IV). The arylsulfur halotetrafluoride is then reacted with a fluoride source to form the arylsulfur pentafluoride having a formula (I).

Scheme 1: (Processes I and II)

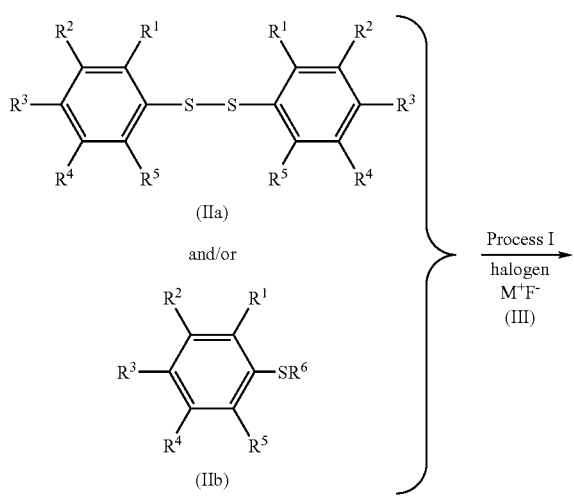

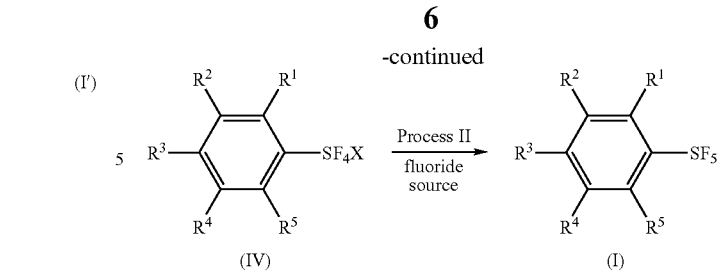

With regard to formulas (I), (IIa), (IIb), (III), and (IV): substituents $R^1$, $R^2$, $R^3$, $R^4$, and $R^5$ each is independently a hydrogen atom; a halogen atom that is a fluorine atom, a chlorine atom, a bromine atom, or an iodine atom; a substituted or unsubstituted alkyl group having from 1 to 18 carbon atoms, preferably from 1 to 10 carbon atoms; a substituted or unsubstituted aryl group having from 6 to 30 carbon atoms, preferably from 6 to 15 carbon atoms; a nitro group; a cyano group; a substituted or unsubstituted alkanesulfonyl group having from 1 to 18 carbon atoms, preferably from 1 to 10 carbon atoms; a substituted or unsubstituted arenesulfonyl group having from 6 to 30 carbon atoms, preferably from 6 to 15 carbon atoms; a substituted or unsubstituted alkoxy group having from 1 to 18 carbon atoms, preferably from 1 to 10 carbon atoms; a substituted or unsubstituted aryloxy group having from 6 to 30 carbon atoms, preferably from 6 to 15 carbon atoms; a substituted or unsubstituted acyloxy group having from 1 to 18 carbon atom, preferably from 1 to 10 carbon atoms; a substituted or unsubstituted alkanesulfonyloxy group having from 1 to 18 carbon atom, preferably from 1 to 10 carbon atoms; a substituted or unsubstituted arenesulfonyloxy group having from 6 to 30 carbon atoms, preferably from 6 to 15 carbon atoms; a substituted or unsubstituted alkoxycarbonyl group having 2 to 18 carbon atoms, preferably from 2 to 10 carbon atoms; a substituted or unsubstituted aryloxycarbonyl group having 7 to 30 carbon atoms, preferably from 7 to 15 carbons; a substituted carbamoyl group having 2 to 18 carbon atoms, preferably from 2 to 10 carbon atoms; a substituted amino group having 1 to 18 carbon atoms, preferably from 1 to 10 carbon atoms; and a $SF_5$ group; and $R^6$ is a hydrogen atom, a silyl group, a metal atom, an ammonium moiety, a phosphonium moiety, or a halogen atom.

With regard to M, M is a metal atom, an ammonium moiety, or a phosphonium moiety, and with regard to X, X is a chlorine atom, a bromine atom, or an iodine atom.

The term "alkyl" as used herein is linear, branched, or cyclic alkyl. The alkyl part of alkanesulfonyl, alkoxy, alkanesulfonyloxy, or alkoxycarbonyl group as used herein is also linear, branched, or cyclic alkyl part. The term "substituted alkyl" as used herein means an alkyl moiety having one or more substituents such as a halogen atom, a substituted or unsubstituted aryl group, and any other group with or without a heteroatom(s) such as an oxygen atom(s), a nitrogen atom(s), and/or a sulfur atom(s), which does not limit reactions of this invention.

The term "substituted aryl" as used herein means an aryl moiety having one or more substituents such as a halogen atom, a substituted or unsubstituted alkyl group, and any other group with or without a heteroatom(s) such as an oxygen atom(s), a nitrogen atom(s), and/or a sulfur atom(s), which does not limit reactions of this invention.

The term "substituted alkanesulfonyl" as used herein means an alkanesulfonyl moiety having one or more substituents such as a halogen atom, a substituted or unsubstituted aryl group, and any other group with or without a heteroatom(s) such as an oxygen atom(s), a nitrogen atom(s), and/or a sulfur atom(s), which does not limit reactions of this invention.

The term "substituted arenesulfonyl" as used herein means an arenesulfonyl moiety having one or more substituents such as a halogen atom, a substituted or unsubstituted alkyl group, and any other group with or without a heteroatom(s) such as an oxygen atom(s), a nitrogen atom(s), and/or a sulfur atom(s), which does not limit reactions of this invention.

The term "substituted alkoxy" as used herein means an alkoxy moiety having one or more substituents such as a halogen atom, a substituted or unsubstituted aryl group, and any other group with or without a heteroatom(s) such as an oxygen atom(s), a nitrogen atom(s), and/or a sulfur atom(s), which does not limit reactions of this invention.

The term "substituted aryloxy" as used herein means an aryloxy moiety having one or more substituents such as a halogen atom, a substituted or unsubstituted alkyl group, and any other group with or without a heteroatom(s) such as an oxygen atom(s), a nitrogen atom(s), and/or a sulfur atom(s), which does not limit reactions of this invention.

The term "substituted acyloxy" as used herein means an acyloxy moiety having one or more substituents such as a halogen atom, a substituted or unsubstituted alkyl group, a substituted or unsubstituted aryl group, and any other group with or without a heteroatom(s) such as an oxygen atom(s), a nitrogen atom(s), and/or a sulfur atom(s), which does not limit reactions of this invention.

The term "substituted alkanesulfonyloxy" as used herein means an alkanesulfonyloxy moiety having one or more substituents such as a halogen atom, a substituted or unsubstituted aryl group, and any other group with or without a heteroatom(s) such as an oxygen atom(s), a nitrogen atom(s), and/or a sulfur atom(s), which does not limit reactions of this invention.

The term "substituted arenesulfonyloxy" as used herein means an arenesulfonyloxy moiety having one or more substituents such as a halogen atom, a substituted or unsubstituted alkyl group, and any other group with or without a heteroatom(s) such as an oxygen atom(s), a nitrogen atom(s), and/or a sulfur atom(s), which does not limit reactions of this invention.

The term "substituted alkoxycarbonyl" as used herein means an alkoxycarbonyl moiety having one or more substituents such as a halogen atom, a substituted or unsubstituted aryl group, and any other group with or without a heteroatom(s) such as an oxygen atom(s), a nitrogen atom(s), and/or a sulfur atom(s), which does not limit reactions of this invention.

The term "substituted aryloxycarbonyl" as used herein means an aryloxycarbonyl moiety having one or more substituents such as a halogen atom, a substituted or unsubstituted alkyl group, and any other group with or without a heteroatom(s) such as an oxygen atom(s), a nitrogen atom(s), and/or a sulfur atom(s), which does not limit reactions of this invention.

The term "substituted carbamoyl" as used herein means a carbamoyl moiety having one or more substituents such as a substituted or unsubstituted alkyl group, a substituted or unsubstituted aryl group, and any other group with or without a heteroatom(s) such as an oxygen atom(s), a nitrogen atom(s), and/or a sulfur atom(s), which does not limit reactions of this invention.

The term "substituted amino" as used herein means an amino moiety having one or more substituents such as a substituted or unsubstituted acyl group, a substituted or unsubstituted alkanesulfonyl group, a substituted or unsubstituted arenesulfonyl group, and any other group with or without a heteroatom(s) such as an oxygen atom(s), a nitrogen atom(s), and/or a sulfur atom(s), which does not limit reactions of this invention.

Among the substituents, $R^1$, $R^2$, $R^3$, $R^4$, and $R^5$, described above, a hydrogen atom, a halogen atom, a substituted or unsubstituted alkyl group, a substituted or unsubstituted aryl group, a nitro group, a cyano group, a substituted or unsubstituted alkanesulfonyl group, a substituted or unsubstituted arenesulfonyl group, a substituted or unsubstituted alkoxy group, a substituted or unsubstituted aryloxy group, a substituted or unsubstituted acyloxy group, and a substituted or unsubstituted alkoxycarbonyl group are preferable, and a hydrogen atom, a halogen atom, a substituted or unsubstituted alkyl group, a substituted or unsubstituted aryl group, and a nitro group are more preferable from the viewpoint of availability of the starting materials.

Note that according to the nomenclature of Chemical Abstract Index Name, and in accordance with the present disclosure, for example, $C_6H_5$—$SF_5$ is named sulfur, pentafluorophenyl-; p-$C_1$-$C_6H_4$—$SF_5$ is named sulfur, (4-chlorophenyl)pentafluoro-; and p-$CH_3$—$C_6H_4$—$SF_5$ is named sulfur, pentafluoro(4-methylphenyl)-. $C_6H_5$—$SF_4Cl$ is named sulfur, chlorotetrafluorophenyl-; p-$CH_3$—$C_6H_4$—$SF_4Cl$ is named sulfur, chlorotetrafluoro(4-methylphenyl)-; and p-$NO_2$—$C_6H_4$—$SF_4Cl$ is named sulfur, chlorotetrafluoro(4-nitrophenyl)-.

Arylsulfur halotetrafluoride compounds of formula (IV) include isomers such as trans-isomers and cis-isomers as shown below; arylsulfur halotetrafluoride is represented by ArSF$_4$X:

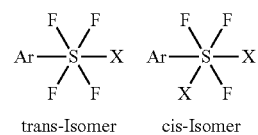

trans-Isomer   cis-Isomer

Table 1 provides structure names and formulas for reference when reviewing Schemes 1, 3~10 and Examples 1~34:

TABLE 1

Formulas (I~V)

| Name | Structure/Formula Number |
|---|---|
| Arylsulfur pentafluoride | (I) |
| Aryl sulfur compound | (IIa) |

TABLE 1-continued

Formulas (I~V)

| Name | Structure/Formula Number |
|---|---|
| Aryl sulfur compound | 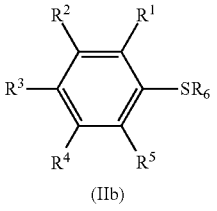<br>(IIb) |
| Fluoro salt | $M^+F^-$<br>(III) |
| Arylsulfur halotetrafluoride | 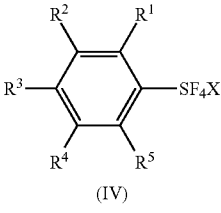<br>(IV) |
| Arylsulfur trifluoride | 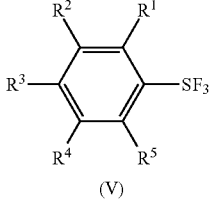<br>(V) |

Process I (Scheme 1)

Process I includes reacting at least one aryl sulfur compound, having a formula (IIa) or (IIb), with a halogen selected from the group of chlorine, bromine, iodine and interhalogens, and a fluoro salt ($M^+F^-$, formula III) to form an arylsulfur halotetrafluoride having a formula (IV).

The substituent(s), $R^1$, $R^2$, $R^3$, $R^4$, and $R^5$, of the products represented by the formula (IV) may be different from the substituent(s), $R^1$, $R^2$, $R^3$, $R^4$, and $R^5$, of the starting materials represented by the formulas (IIa) and/or (IIb). Thus, embodiments of this invention include transformation of the $R^1$, $R^2$, $R^3$, $R^4$, and $R^5$ to different $R^1$, $R^2$, $R^3$, $R^4$, and $R^5$ which may take place during the reaction of the present invention or under the reaction conditions as long as the —S—S- or —S- moiety is transformed to a —SF$_4$X group(s).

Illustrative aryl sulfur compounds, as represented by formula (IIa), of the invention include, but are not limited to: diphenyl disulfide, each isomer of bis(fluorophenyl)disulfide, each isomer of bis(difluorophenyl)disulfide, each isomer of bis(trifluorophenyl)disulfide, each isomer of bis(tetrafluorophenyl)disulfide, bis(pentafluorophenyl)disulfide, each isomer of bis(chlorophenyl)disulfide, each isomer of bis(dichlorophenyl)disulfide, each isomer of bis(trichlorophenyl)disulfide, each isomer of bis(bromophenyl)disulfide, each isomer of bis(dibromophenyl)disulfide, each isomer of bis(iodophenyl)disulfide, each isomer of bis(chlorofluorophenyl)disulfide, each isomer of bis(bromofluorophenyl)disulfide, each isomer of bis(bromochlorophenyl)disulfide, each isomer of bis(fluoroiodophenyl)disulfide, each isomer of bis(tolyl)disulfide, each isomer of bis[(methoxymethyl)phenyl]disulfide, each isomer of bis{[(cyclohexyloxy)methyl]phenyl}disulfide, each isomer of bis[(phenylmethyl)phenyl]disulfide, each isomer of bis[(cyanomethyl)phenyl] disulfide, each isomer of bis[(nitromethyl)phenyl]disulfide, each isomer of bis{[(methanesulfonyl)methyl] phenyl}disulfide, each isomer of bis{[(benzenesulfonyl)ethyl]phenyl}disulfide, each isomer of bis(ethylphenyl)disulfide, each isomer of bis[(methoxyethyl)phenyl]disulfide, each isomer of bis[(nitroethyl)phenyl]disulfide, each isomer of bis[(phenylethyl)phenyl]disulfide, each isomer of bis [chloro(methyl)phenyl]disulfide, bis[bromo(methyl)phenyl]disulfide, each isomer of bis[(trifluoromethyl)phenyl]disulfide, each isomer of bis(dimethylphenyl)disulfide, each isomer of bis[chloro(dimethyl)phenyl]disulfide, each isomer of bis[di(trifluoromethyl)phenyl]disulfide, each isomer of bis(trimethylphenyl)disulfide, each isomer of bis[chloro(trimethyl)phenyl]disulfide, each isomer of bis(tetramethylphenyl) disulfide, each isomer of bis[chloro(tetramethyl)phenyl] disulfide, bis(pentamethylphenyl)disulfide, each isomer of bis(ethylphenyl)disulfide, each isomer of bis[(2,2,2-trifluoroethyl)phenyl]disulfide, each isomer of bis[(perfluoroethyl)phenyl]disulfide, each isomer of bis(diethylphenyl)disulfide, each isomer of bis(ethylmethylphenyl)disulfide, each isomer of bis(propylphenyl)disulfide, each isomer of bis(isopropylphenyl)disulfide, each isomer of bis(butylphenyl)disulfide, each isomer of bis(sec-butylphenyl)disulfide, each isomer of bis(isobutylphenyl)disulfide, each isomer of bis(tert-butylphenyl)disulfide, each isomer of bis(cyclopropylphenyl) disulfide, each isomer of bis(cyclopentylphenyl)disulfide, each isomer of bis(cyclohexylphenyl)disulfide, each isomer of bis{[(cyclohexyl)cyclohexyl]phenyl}disulfide, each isomer of bis(biphenyl)disulfide, each isomer of bis(tolylphenyl)disulfide, each isomer of bis[(chlorophenyl)phenyl]disulfide, each isomer of bis[(bromophenyl)phenyl]disulfide, each isomer of bis[(nitrophenyl)phenyl]disulfide, each isomer of bis(terphenylyl)disulfide, each isomer of bis[(phenyl)terphenylyl]disulfide, each isomer of bis[(methanesulfonyl)phenyl]disulfide, each isomer of bis [(trifluoromethanesulfonyl)phenyl]disulfide, each isomer of bis[(benzenesulfonyl)phenyl]disulfide, each isomer of bis [(toluenesulfonyl)phenyl]disulfide, each isomer of bis(methoxyphenyl)disulfide, each isomer of bis(ethoxyphenyl)disulfide, each isomer of bis(propoxyphenyl)disulfide, each isomer of bis(butoxyphenyl)disulfide, each isomer of bis(cyclopropylphenyl)disulfide, bis(cyclohexyloxylphenyl)disulfide, each isomer of bis[(trifluoromethoxy)phenyl]disulfide, each isomer of bis[(perfluoroethoxy)phenyl]disulfide, each isomer of bis[(trifluoroethoxy)phenyl]disulfide, each isomer of bis[(tetrafluoroethoxy)phenyl]disulfide, each isomer of bis [(perfluoropropoxy)phenyl]disulfide, each isomer of bis(phenyloxyphenyl)disulfide, each isomer of bis(fluorophenyloxyphenyl)disulfide, each isomer of bis (chlorophenyloxyphenyl)disulfide, each isomer of bis (bromophenyloxyphenyl)disulfide, each isomer of bis (nitrophenyloxyphenyl)disulfide, each isomer of bis [(dinitrophenyloxy)phenyl]disulfide, each isomer of bis [(pentafluorophenyloxy)phenyl]disulfide, each isomer of bis (trifluoromethylphenyloxyphenyl)disulfide, each isomer of bis(cyanophenyloxyphenyl)disulfide, each isomer of bis (naphthyloxylphenyl)disulfide, each isomer of bis[(heptafluoronaphthyloxy)phenyl]disulfide, each isomer of bis[acetoxyphenyl]disulfide, each isomer of bis[(benzoyloxy) phenyl]disulfide, each isomer of bis[(methanesulfonyloxy) phenyl]disulfide, each isomer of bis[(benzenesulfonyloxy) phenyl]disulfide, each isomer of bis[(toluenesulfonyloxy) phenyl]disulfide, each isomer of bis[(methoxycarbonyl) phenyl]disulfide, each isomer of bis[(ethoxycarbonyl) phenyl]disulfide, each isomer of bis[(phenoxycarbonyl) phenyl]disulfide, each isomer of bis[(N,N-dimethylcarbamoyl)phenyl]disulfide, each isomer of bis[(N, N-diethylcarbamoyl)phenyl]disulfide, each isomer of bis[(N, N-diphenylcarbamoyl)phenyl]disulfide, each isomer of bis[(N,N-dibenzylcarbamoyl)phenyl]disulfide, each isomer of bis[(N-acetyl-N-methylamino)phenyl]disulfide, each isomer of bis[(N-acetyl-N-phenylamino)phenyl]disulfide, each isomer of bis[(N-acetyl-N-benzylamino)phenyl]disulfide, each isomer of bis[(N-benzoyl-N-methylamino)phenyl]disulfide, each isomer of bis[(N-methanesulfonyl-N-methylamino) phenyl]disulfide, each isomer of bis[(N-toluenesulfonyl-N-methylamino)phenyl]disulfide, each isomer of bis[(N-toluenesulfonyl-N-benzylamino)phenyl]disulfide, and each isomer of bis[(pentafluorosulfanyl)phenyl]disulfide. Each of the above formula (IIa) compounds is available (see for example Sigma, Acros, TCI, Lancaster, Alfa Aesar, etc.) or can be prepared in accordance with understood principles of synthetic chemistry.

Illustrative aryl sulfur compounds, as represented by formula (IIb), of the invention include, but are not limited to: benzenethiol, each isomer of fluorobenzenethiol (o-, m-, and p-fluorobenzenethiol), each isomer of chlorobenzenethiol, each isomer of bromobenzenethiol, each isomer of iodobenzenethiol, each isomer of difluorobenzenethiol, each isomer of trifluorobenzenethiol, each isomer of tetrafluorobenzenethiol, pentafluorobenzenethiol, each isomer of dichlorobenzenethiol, each isomer of chlorofluorobenzenethiol, each isomer of methylbenzenethiol, each isomer of (trifluoromethyl)benzenethiol, each isomer of dimethylbenzenethiol, each isomer of bis(trifluoromethyl)benzenethiol, each isomer of methyl(trifluoromethyl)benzenethiol, each isomer of trimethylbenzenethiol, each isomer of tetramethylbenzenethiol, pentamethylbenzenethiol, each isomer of ethylbenzenethiol, each isomer of (2,2,2-trifluoroethyl)benzenethiol, each isomer of (perfluoroethyl)benzenethiol, each isomer of diethylbenzenethiol, each isomer of ethylmethylbenzenethiol, each isomer of propylbenzenethiol, each isomer of isopropylbenzenethiol, each isomer of butylbenzenethiol, each isomer of sec-butylbenzenethiol, each isomer of isobutylbenzenethiol, each isomer of tert-butylbenzenethiol, each isomer of nitrobenzenethiol, each isomer of dinitrobenzenethiol, each isomer of cyanobenzenethiol, each isomer of phenylbenzenethiol, each isomer of tolylbenzenethiol, each isomer of (chlorophenyl)benzenethiol, each isomer of (bromophenyl)benzenethiol, each isomer of (nitrophenyl)benzenethiol, each isomer of (methanesulfonyl)benzenethiol, each isomer of (trifluoromethanesulfonyl)benzenethiol, each isomer of (benzenesulfonyl)benzenethiol, each isomer of (toluenesulfonyl)benzenethiol, each isomer of (methoxycarbonyl)benzenethiol, each isomer of (ethoxycarbonyl)benzenethiol, each isomer of (phenoxycarbonyl)benzenethiol, each isomer of (N,N-dimethylcarbamoyl)benzenethiol, each isomer of (N,N-diethylcarbamoyl) benzenethiol, each isomer of (N,N-dibenzylcarbamoyl) benzenethiol, each isomer of (N,N-diphenylcarbamoyl) benzenethiol, each isomer of (N-acetyl-N-methylamino) benzenethiol, each isomer of (N-acetyl-N-phenylamino) benzenethiol, each isomer of (N-acetyl-N-benzylamino) benzenethiol, each isomer of (N-benzoyl-N-methylamino) benzenethiol, each isomer of (N-methanesulfonyl-N-methylamino)benzenethiol, each isomer of (N-toluenesulfonyl-N-methylamino)benzenethiol, each isomer of (N-toluenesulfonyl-N-benzylamino)benzenethiol, and each isomer of (pentafluorosulfanyl)benzenethiol; lithium, sodium, and potassium salts of the benzenethiol compounds exemplified here; ammonium, diethylammonium, triethylammonium, trimethylammnoim, tetramethylammonium, tetraethylammonium, tetrapropylammonium, and tetrabutylammonium salts of the benzenethiol compounds exemplified here; tetramethylphosphonium, tetraethylphosphonium, tetrapropylphosphonium, tetrabutylphosphonium, and tetraphenylphosphonium salts of the benzenethiol compounds exemplified here; and S-trimethylsilyl, S-triethylsilyl, S-tripropylsilyl, S-dimethyl-t-butylsilyl, and S-dimethylphenylsilyl derivative of the benzenethiol compounds exemplified here. Examples of aryl sulfur compounds of formula (IIb) where $R^6$ is a halogen atom are benzenesulfenyl chloride, each isomer of nitrobenzenesulfenyl chloride, each isomer of dinitrobenzenesulfenyl chloride, and other like compounds. Each of the above formula (IIb) compounds is available (see for example Sigma, Acros, TCI, Lancaster, Alfa Aesar, etc.) or can be prepared in accordance with understood principles of synthetic chemistry.

Typical halogens employable in the present invention include chlorine ($Cl_2$), bromine ($Br_2$), iodine ($I_2$), and interhalogens such as ClF, BrF, ClBr, ClI, $Cl_3I$, and BrI. Among these, chlorine ($Cl_2$) is preferable due to low cost.

Fluoro salts, having a formula (III), are those which are easily available and are exemplified by metal fluorides, ammonium fluorides, and phosphonium fluorides. Examples of suitable metal fluorides are alkali metal fluorides such as lithium fluoride, sodium fluoride, potassium fluoride (including spray-dried potassium fluoride), rubidium fluoride, and cesium fluoride. Examples of suitable ammonium fluorides are tetramethylammonium fluoride, tetraethylammonium fluoride, tetrapropylammonium fluoride, tetrabutylammonium fluoride, benzyltrimethylammonium fluoride, benzyltriethylammonium fluoride, and so on. Examples of suitable phosphonium fluorides are tetramethylphosphonium fluoride, tetraethylphosphonium fluoride, tetrapropylphosphonium fluoride, tetrabutylphosphonium fluoride, tetraphenylphosphonium fluoride, tetratolylphosphonium fluoride, and so on. The alkali metal fluorides, such as potassium fluoride and cesium fluoride, are preferable from the viewpoint of availability and capacity to result in high yield, and potassium fluoride is most preferable from the viewpoint of cost.

As a fluoro salt (formula III), there can be used a mixture of a metal fluoride and an ammonium fluoride or a phosphonium fluoride, a mixture of an ammonium fluoride and a phosphonium fluoride, and a mixture of a metal fluoride, an ammonium fluoride, and a phosphonium fluoride.

As a fluoro salt (formula III), there can also be used a mixture of a metal fluoride and an ammonium salt having an anion part other than $F^-$; a mixture of a metal salt having an anion part other than $F^-$ and an ammonium fluoride; a mixture of a metal fluoride and a phosphonium salt having an anion part other than $F^-$; a mixture of a metal salt having an anion part other than $F^-$ and a phosphonium fluoride; a mixture of an ammonium fluoride and a phosphonium salt having an anion part other than $F^-$; and a mixture of an ammonium salt having an anion part other than $F^-$ and a phosphonium fluoride. Furthermore, there can be used a mixture of a metal fluoride, an ammonium fluoride, and a phosphonium salt having an anion part other than $F^-$; a mixture of a metal fluoride, an ammonium salt having an anion part other than $F^-$, and a phosphonum fluoride; a mixture of a metal salt having an anion part other than $F^-$, an ammonium fluoride, and a phosphonium fluoride; a mixture of a metal fluoride, an ammonium salt having an anion part other than $F^-$, and a phosphonium salt having an anion part other than $F^-$; and so on. These salts can undertake a mutual exchange reaction of the anion parts between and among these salts (for example, see Scheme 2).

Scheme 2: Mutual anion exchange reaction between salts

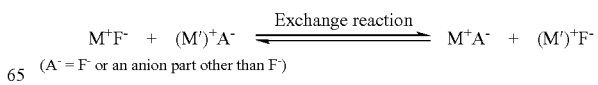

$M^+F^-$ + $(M')^+A^-$ $\rightleftharpoons$ $M^+A^-$ + $(M')^+F^-$ ($A^-$ = $F^-$ or an anion part other than $F^-$)

The combination of these salts may accelerate the reactions in Process I, because the reaction may depend on the solubility of the fluoro salts to the solvent used. As such, a high concentration of fluoride anions ($F^-$) will increase the available fluoride anion during the reaction. Therefore, one may choose a suitable combination of these salts in order to increase the effective concentration of $F^-$. The amount (used against the amount of the metal fluoride, ammonium fluorides, and/or phosphonium fluorides) of the metal, ammonium, and phosphonium salts having anion parts other than $F^-$ can be chosen from the catalytic amounts to any amounts that do not interfere with the reactions or do not so decrease the yields of the products. The anion parts other than $F^-$ can be chosen from any anions which do not limit the reactions or do not so decrease the yields of the products. The examples of the anion parts other than $F^-$ are, but are not limited to, $Cl^-$, $Br^-$, $I^-$, $BF_4^-$, $PF_6^-$, $SO_4^-$, $^-OCOCH_3$, $^-OCOCF_3$, $^-OSO_2CH_3$, $^-OSO_2CF_3$, $^-OSO_2C_4F_9$, $^-OSO_2C_6H_5$, $^-OSO_2C_6H_4CH_3$, $^-OSO_2C_6H_4Br$, and so on. Among them, the anion parts (other than $F^-$) which do not have an oxygen anion(s) are preferable, and $Cl^-$, $BF_4^-$ and $PF_6^-$ are more preferable because of high yield reactions. In addition, $Cl^-$ is most preferable because of the cost.

From the viewpoint of efficiency and yields of the reactions, Process I is preferably carried out in the presence of one or more solvents. The solvent is preferably an inert, polar, aprotic solvent. The preferable solvents will not substantially react with the starting materials and reagents, the intermediates, and the final products. Suitable solvents include, but are not limited to, nitriles, ethers, nitro compounds, and so on, and mixtures thereof. Illustrative nitriles are acetonitrile, propionitrile, benzonitrile, and so on. Illustrative ethers are tetrahydrofuran, diethyl ether, dipropyl ether, dibutyl ether, t-butyl methyl ether, dioxane, glyme, diglyme, triglyme, and so on. Illustrative nitro compounds are nitromethane, nitroethane, nitropropane, nitrobenzene, and so on. Acetonitrile is a preferred solvent for use in Process I from a viewpoint of providing higher yields of the products.

In order to obtain good yields of product in Process I, the reaction temperature can be selected in the range of about −60° C.~+70° C. More preferably, the reaction temperature can be selected in the range of about −40° C.~+50° C. Furthermore preferably, the reaction temperature can be selected in the range of about −20° C.~+40° C.

Reaction conditions of Process I are optimized to obtain economically good yields of product. In one illustrative embodiment, from about 5 mol to about 20 mol of halogen are combined with about 1 mol of aryl sulfur compound (formula IIa) to obtain a good yield of arylsulfur halotetrafluorides (formula IV). In another embodiment, from about 3 to about 12 mol of halogen are combined with 1 mol of aryl sulfur compound of formula IIb ($R^6$=a hydrogen atom, a silyl group, a metal atom, an ammonium moiety, or a phosphonium moiety) to obtain good yields of arylsulfur halotetrafluorides (formula IV). From about 2 to about 8 mol of halogen are combined with 1 mol of aryl sulfur compound of formula IIb ($R^6$=a halogen atom) to obtain good yields of arylsulfur halotetrafluorides (formula IV). The amount of a fluoro salt (formula III) used in embodiments of Process I can be in the range of from about 8 to about 24 mol against 1 mol of aryl sulfur compound of formula (IIa) to obtain economically good yields of product. The amount of a fluoro salt (formula III) used in embodiments of Process I can be in the range of from about 4 to about 12 mol against 1 mol of aryl sulfur compound of formula (IIb) to obtain economically good yields of product.

Note that the reaction time for Process I varies dependent upon reaction temperature, and the types and amounts of substrates, reagents, and solvents. As such, reaction time is generally determined as the amount of time required to complete a particular reaction, but can be from about 0.5 h to several days, preferably, within a few days.

Scheme 3: Reaction mechanism for Process I

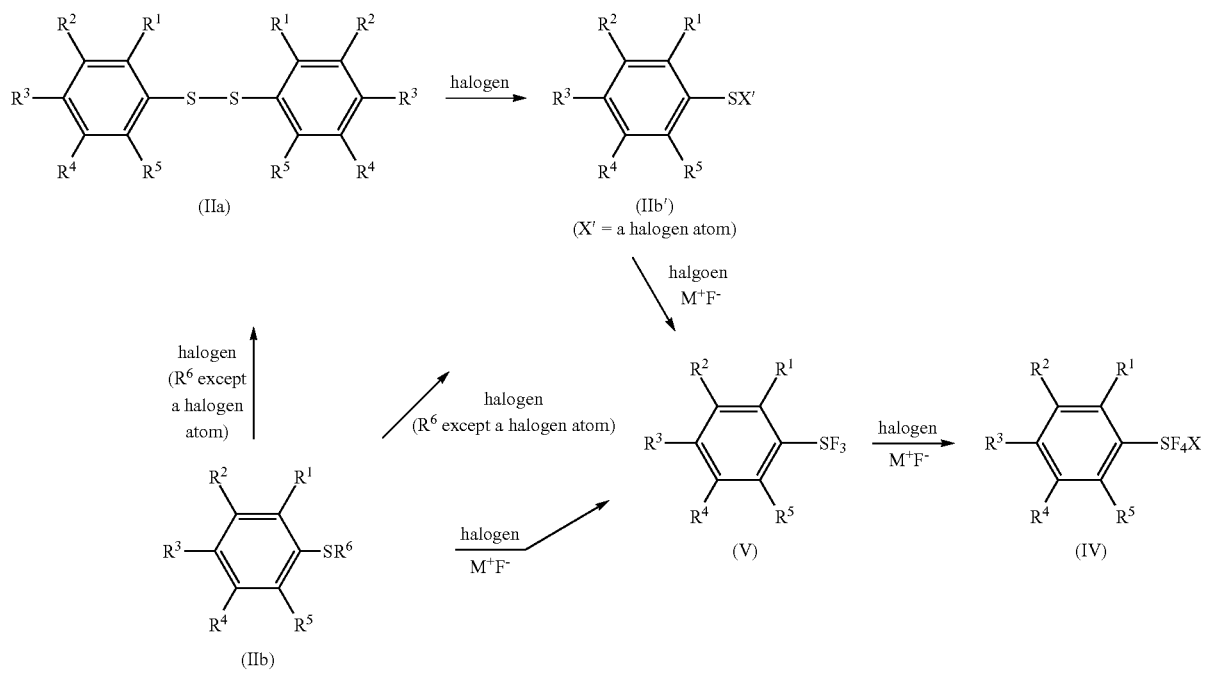

A more complete reaction mechanism of Process I is shown in Scheme 3 above. Aryl sulfur compound of formula (IIa) reacts with halogen to form arylsulfur halide (IIb'=IIb when $R^6$=a halogen atom), which then reacts with halogen and fluoro salt ($M^+F^-$) to form arylsulfur trifluoride (formula V). The arylsulfur trifluoride further reacts with halogen and fluoro salt to give the arylsulfur halotetrafluoride (formula (IV)). As such, the compounds as represented by formula (V) act as intermediates in the formation of compounds of formula (IV). The compounds as represented by formula (IIb') also act as intermediates. The starting aryl sulfur compound of formula (IIb when $R^6$=a halogen atom) reacts with halogen and fluoro salt to form the arylsulfur trifluoride. Aryl sulfur compounds as represented by formula (IIb when $R^6$=a hydrogen atom, a metal atom, an ammonium moiety, or a phosphonium moiety) react with halogen to form aryl sulfur compounds as represented by formula (IIa) or formula (IIb'), which then reacts with halogen and fluoro salt to give the arylsulfur trifluoride (formula V). As such, the compounds as represented by formula (IIa) or (IIb') act as intermediates in the formation of compounds of formula (IV) from aryl sulfur compounds of formula (IIb, $R^6$ except for a halogen atom). The reaction mechanism for the production of arylsulfur halotetrafluoride (formula IV) via arylsulfur trifluoride (formula V) was confirmed by $^{19}F$ NMR of an intermediate reaction mixture. In addition, the arylsulfur trifluoride can be converted to the arylsulfur halotetrafluoride (formula IV) under the similar reaction conditions as demonstrated by at least Example 14.

Process II (Scheme 1)

Embodiments of the invention include Process II: a reaction of arylsulfur halotetrafluoride, obtained by the process I, with a fluoride source, as shown in Scheme 1.

The substituent(s), $R^1$, $R^2$, $R^3$, $R^4$, and $R^5$, of the products represented by the formula (I) may be different from the substituent(s), $R^1$, $R^2$, $R^3$, $R^4$, and $R^5$, of the materials represented by the formula (IV). Thus, embodiments of this invention include transformation of the $R^1$, $R^2$, $R^3$, $R^4$, and $R^5$ to different $R^1$, $R^2$, $R^3$, $R^4$, and $R^5$ which may take place during the reaction of the present invention or under the reaction conditions as long as the —$SF_4X$ is transformed to a —$SF_5$ group.

Fluoride sources employable in Process II are anhydrous compounds that display fluoride activity to the arylsulfur halotetrafluoride (formula IV). The fluoride sources can be selected from fluorides of typical elements in the Periodic Table, fluorides of transition elements in the Periodic Table, and mixture or compounds between or among these fluorides of typical elements and/or transition elements. The fluoride source may be a mixture, salt, or complex with an organic molecule(s) that does (do) not limit the reactions of this invention. The fluoride sources also include mixtures or compounds of fluoride sources with fluoride source-activating compounds such as $SbCl_5$, $AlCl_3$, $PCl_5$, $BCl_3$, and so on. Process II can be carried out using one or more fluoride sources.

Suitable examples of fluorides of the typical elements include fluorides of Element 1 in the Periodic Table such as hydrogen fluoride (HF) and alkali metal fluorides, LiF, NaF, KF, RbF, and CsF; fluorides of Element 2 (alkaline earth metal fluorides) such as $BeF_2$, $MgF_2$, $MgFCl$, $CaF_2$, $SrF_2$, $BaF_2$ and so on; fluorides of Element 13 such as $BF_3$, $BF_2Cl$, $BFCl_2$, $AlF_3$, $AlF_2Cl$, $AlFCl_2$, $GaF_3$, $InF_3$, and so on; fluorides of Element 14 such as $SiF_4$, $SiF_3Cl$, $SiF_2Cl_2$, $SiFCl_3$, $GeF_4$, $GeF_2Cl_2$, $SnF_4$, $PbF_2$, $PbF_4$, and so on; fluorides of Element 15 such as $PF_5$, $AsF_5$, $SbF_3$, $SbF_5$, $SbF_4Cl$, $SbF_3Cl_2$, $SbF_2Cl_3$, $SbFCl_4$, $BiF_5$, and so on; fluorides of Element 16 such as $OF_2$, $SeF_4$, $SeF_6$, $TeF_4$, $TeF_6$, and so on; fluorides of Element 17 such as $F_2$, $ClF$, $ClF_3$, $BrF$, $BrF_3$, $IF_5$, and so on.

Suitable examples of fluorides of the transition elements (transition meal fluorides) include fluorides of Element 3 in the Periodic Table such as $ScF_3$, $YF_3$, $LaF_3$, and so on; fluorides of Element 4 such as $TiF_4$, $ZrF_3$, $ZrF_4$, $HfF_4$, and so on; fluorides of Element 5 such as $VF_3$, $VF_5$, $NbF_5$, $TaF_5$, and so on; fluorides of Element 6 such as $CrF_3$, $MoF_6$, $WF_6$, and so on; fluorides of Element 7 such as $MnF_2$, $MnF_3$, $ReF_6$, and so on; fluorides of Element 8 such as $FeF_3$, $RuF_3$, $RuF_4$, $OsF_4$, $OsF_5$, $OsF_6$, and so on; fluorides of Element 9 such as $CoF_2$, $CoF_3$, $RhF_3$, $IrF_6$, and so on; fluorides of Element 10 such as $NiF_2$, $PdF_2$, $PtF_2$, $PtF_4$, $PtF_6$, and so on; fluorides of Element 11 such as $CuF_2$, $CuFCl$, $AgF$, $AgF_2$, and so on; fluorides of Element 12 such as $ZnF_2$, $ZnFCl$, $CdF_2$, $HgF_2$, and so on.

Suitable examples of mixture or compounds between or among the fluorides of typical elements and/or transition elements include, but are not limited to, $HBF_4$ [a compound of hydrogen fluoride (HF) and $BF_3$], $HPF_6$, $HAsF_6$, $HSbF_6$, LiF/HF [a mixture or salt of lithium fluoride(LiF) and hydrogen fluoride(HF)], NaF/HF, KF/HF, CsF/HF, $(CH_3)_4NF/HF$, $(C_2H_5)_4NF/HF$, $(C_4H_9)_4NF/HF$, $ZnF_2/HF$, $CuF_2/HF$, $SbF_5/SbF_3$, $SbF_5/SbF_3/HF$, $ZnF_2/SbF_5$, $ZnF_2/SbF_5/HF$, $KF/SbF_5$, $KF/SbF_5/HF$, and so on.

Suitable examples of mixtures, salts, or complexes of the fluorides with organic molecules include, but are not limited to, $BF_3$ diethyl etherate [$BF_3.O(C_2H_5)_2$], $BF_3$ dimethyl etherate, $BF_3$ dibutyl etherate, $BF_3$ tetrahydrofuran complex, $BF_3$ acetonitrile complex ($BF_3.NCCH_3$), $HBF_4$ diethyl etherate, HF/pyridine (a mixture of hydrogen fluoride and pyridine), HF/methylpyridine, HF/dimethylpyridine, HF/trimethylpyridine, HF/trimethylamine, HF/triethylamine, HF/dimethyl ether, HF/diethyl ether, and so on. As HF/pyridine, a mixture of about 70 wt % hydrogen fluoride and about 30 wt % pyridine is preferable because of availability.

Among these examples of fluoride sources mentioned above, transition metal fluorides, fluorides of the Elements 13~15, hydrogen fluoride, and mixtures or compounds thereof, and mixtures, salts, or complexes of these fluorides with organic molecules are preferable.

Among the transition metal fluorides, the fluorides of Elements 11 (Cu, Ag, Au) and 12 (Zn, Cd, Hg) are exemplified preferably. $ZnF_2$ and $CuF_2$ are furthermore preferable from the viewpoint of practical operation, yields, and cost. Among the fluorides of the Elements 13~15, $BF_3$, $AlF_3$, $AlF_2Cl$, $SbF_3$, $SbF_5$, $SbF_4Cl$, and $SbF_3Cl_2$ are preferably exemplified. Fluorides of Elements 13~15 can be used preferably for the preparation of polyfluorinated arylsulfur pentafluorides. Among the organic molecules usable for the mixtures, salts, or complexes with the fluorides, pyridine, ethers such as dimethyl ether, diethyl ether, dipropyl ether, and diisopropyl ether, alkylamines such as trimethylamine and triethylamine, and nitriles such as acetonitrile and propionitrile are preferable. Among these, pyridine, diethyl ether, triethylamine, and acetonitrile are more preferable because of availability and cost.

In some cases, since the reaction of an arylsulfur halotetrafluoride and a fluoride source can be slowed down by flowing an inactive gas such as nitrogen (see Examples 18 and 19), it is not preferable that the vapor on the reaction mixture and/or the gas which may be generated from the reaction mixture be removed, for example by flowing an inactive gas on or through the reaction mixture or other methods. This was an unexpected finding discovered by the inventor, as one would not expect removal of the reaction vapor to slow the reaction. Therefore, there is a case that it is preferable that the reaction be carried out in a closed or sealed reactor, by maintaining the reactor at a constant pressure, or by equipping the reactor with a balloon filled with an inactive gas such as nitrogen, or in any other like manner. In this manner, embodiments of the invention facilitate the presence of the reaction vapor.

Process II can be carried out with or without a solvent. However, in many cases, unlike most organic reactions, the present invention typically does not require a solvent. This presents an added advantage to performing embodiments of the invention (due to lower cost, no solvent separating requirements, etc). In some cases, the use of solvent is preferable for mild and efficient reactions. Where a solvent is utilized, alkanes, halocarbons, ethers, nitriles, nitro compounds can be used. Example alkanes include normal, branched, cyclic isomers of pentane, hexane, heptane, octane, nonane, decane, dodecan, undecane, and other like compounds. Illustrative halocarbons include dichloromethane, chloroform, carbon tetrachloride, dichloroethane, trichloroethane, terachloroethane, trichlorotrifluoroethane, chlorobenzene, dichlorobenzene, trichlorobenzene, hexafluorobenzene, benzotrifluoride, bis(trifluoromethyl)benzene, perfluorohexane, perfluorocyclohexane, perfluoroheptane, perfluorooctane, perfluorononane, perfluorodecane, perfluorodecalin, and other like compounds. Illustrative ethers include diethyl ether, dipropyl ether, di(isopropyl)ether, dibutyl ether, t-butyl methyl ether, dioxane, glyme (1,2-dimethoxyethane), diglyme, triglyme, and other like compounds. Illustrative nitriles include acetonitrile, propionitrile, benzonitrile, and other like compounds. Illustrative nitro compounds include nitromethane, nitroethane, nitrobenzene, and other like compounds. Where the fluoride source used for the reaction is liquid, it can be used as both a reactant and a solvent. A typical example of this is hydrogen fluoride and a mixture of hydrogen fluoride and pyridine. Hydrogen fluoride and a mixture of hydrogen fluoride and pyridine may be usable as a solvent.

In order to optimize yield with regard to Process II, the reaction temperature is selected in the range of from about −100° C. to about +250° C. More typically, the reaction temperature is selected in the range of from about −80° C. to about +230° C. Most typically, the reaction temperature is selected in the range of from about −60° C. to about +200° C.

In order to obtain economically good yields of the products, the amount of a fluoride source which provides n number of reactive fluoride (employable for the reaction) per molecule can be selected in the range of from about 1/n to about 20/n mol against 1 mol of arylsulfur halotetrafluoride (see formula IV). More typically, the amount can be selected in the range of from about 1/n to about 10/n mol from the viewpoint of yield and cost, as less amounts of a fluoride source decrease the yield(s) and additional amounts of a fluoride source do not significantly improve the yield(s).

As described in Process I, the reaction time of Process II also varies dependent on reaction temperature, the substrates, reagents, solvents, and their amounts used. Therefore, one can modify reaction conditions to determine the amount of time necessary for completing the reaction of Process II, but can be from about 0.1 h to several days, preferably, within a few days.

Embodiments of the invention include processes which comprise (see for example Scheme 4, Processes I and II') reacting at least one aryl sulfur compound having a formula (IIa) or a formula (IIb) with a halogen selected from the group of chlorine, bromine, iodine, and interhalogens, and a fluoro salt having a formula (III), to form an arylsulfur halotetrafluoride, represented by formula (IV). The arylsulfur halotetrafluoride is then reacted with a fluoride source in the presence of a halogen selected from the group of chlorine, bromine, iodine, and interhalogens to form the arylsulfur pentafluoride as represented by a formula (I).

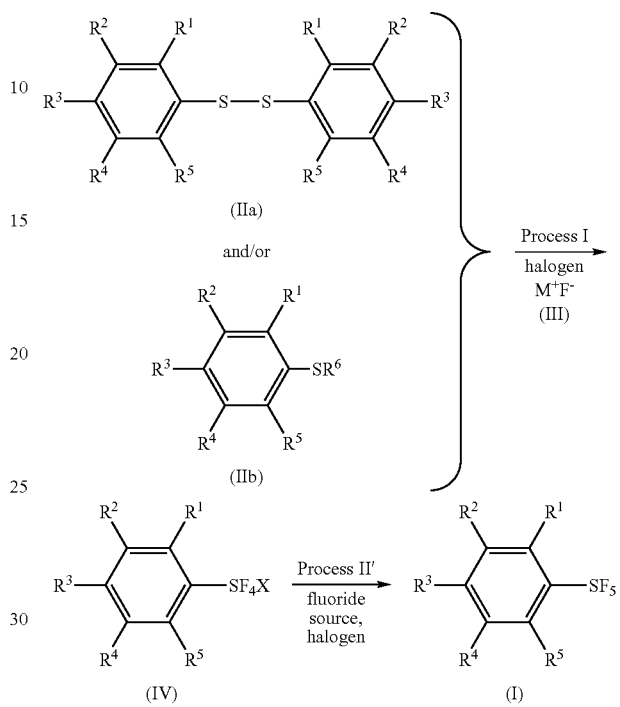

Process I is as described above.

Process II' is the same as Process II above except for the following modifications: The reaction of an arylsulfur halotetrafluoride and a fluoride source can be accelerated by a halogen selected from the group of chlorine, bromine, iodine, and interhalogens (see Examples 15~17).

The substituent(s), $R^1$, $R^2$, $R^3$, $R^4$, and $R^5$, of the products represented by the formula (I) may be different from the substituent(s), $R^1$, $R^2$, $R^3$, $R^4$, and $R^5$, of the materials represented by the formula (IV). Thus, embodiments of this invention include transformation of the $R^1$, $R^2$, $R^3$, $R^4$, and $R^5$ to different $R^1$, $R^2$, $R^3$, $R^4$, and $R^5$ which may take place during the reaction of the present invention or under the reaction conditions as long as the —SF$_4$X is transformed to a —SF$_5$ group.

The acceleration of the reactions by the presence of a halogen in some cases was an unexpected and surprising finding as discovered by the inventor. While not wanting to be tied to a particular mechanism, it is believed that the halogen activates a fluoride source and/or prevents disproportionation of an arylsulfur halotetrafluoride (formula IV) which may occur during this reaction. Therefore, other fluoride source-activating and/or disproportionation-preventing compounds are within the scope of the invention. The reaction in the presence of the halogen may be carried out by methods such as by adding a halogen to the reaction mixture, dissolving a halogen in the reaction mixture, flowing a halogen gas or vapor into the reaction mixture or the reactor, or others like means. Among the halogens, chlorine (Cl$_2$) is preferable because of cost.

The amount of halogen is from a catalytic amount to an amount in large excess. From the viewpoint of cost, a catalytic amount to 5 mol of the halogen, can be preferably selected against 1 mol of arylsulfur halotetrafluoride (formula IV).

Embodiments of the present invention include a process (Process III) which comprises reacting an arylsulfur trifluoride having a formula (V) with a halogen (chlorine, bromine, iodine, or interhalogens) and a fluoro salt having a formula (III) to form an arylsulfur halotetrafluoride having a formula (IV) and (Process II) reacting the obtained arylsulfur halotetrafluoride with a fluoride source to form the arylsulfur pentafluoride having a formula (I). Scheme 5 showing Processes III and II are shown as follows:

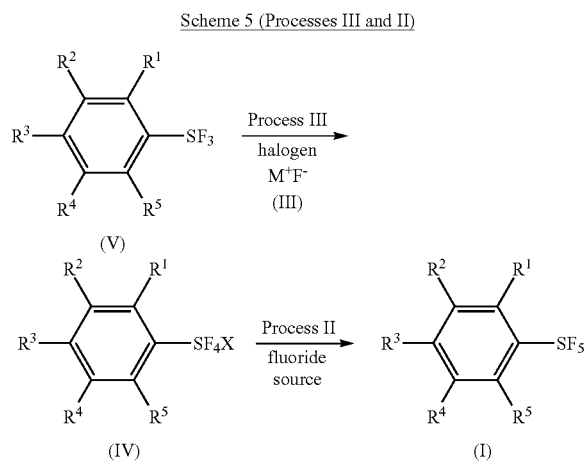

Scheme 5 (Processes III and II)

With regard to formulas (I), (III), (IV), and (V), $R^1$, $R^2$, $R^3$, $R^4$, $R^5$, $R^6$, M and X have the same meaning as defined above.

Process III (Scheme 5)

Embodiments of the present invention provide processes for producing arylsulfur pentafluorides (formula I) by reacting an arylsulfur trifluoride having a formula (V) with a halogen selected from the group of chlorine, bromine, iodine, and interhalogens and a fluoro salt (formula III) to form an arylsulfur halotetrafluoride having a formula (IV).

The substituent(s), $R^1$, $R^2$, $R^3$, $R^4$, and $R^5$, of the products represented by the formula (IV) may be different from the substituent(s), $R^1$, $R^2$, $R^3$, $R^4$, and $R^5$, of the starting materials represented by the formula (V). Thus, embodiments of this invention include transformation of the $R^1$, $R^2$, $R^3$, $R^4$, and $R^5$ to different $R^1$, $R^2$, $R^3$, $R^4$, and $R^5$ which may take place during the reaction of the present invention or under the reaction conditions as long as the —$SF_3$ is transformed to a —$SF_4X$.

Illustrative arylsulfur trifluorides, as represented by formula (V), of the invention can be prepared as described in the literature [see J. Am. Chem. Soc., Vol. 84 (1962), pp. 3064-3072, and Synthetic Communication. Vol. 33 (2003), pp. 2505-2509] and are exemplified, but are not limited, by phenylsulfur trifluoride, each isomer of fluorophenylsulfur trifluoride, each isomer of difluorophenylsulfur trifluoride, each isomer of trifluorophenylsulfur trifluoride, each isomer of tetrafluorophenylsulfur trifluoride, pentafluorophenylsulfur trifluoride, each isomer of chlorophenylsulfur trifluoride, each isomer of bromophenylsulfur trifluoride, each isomer of chlorofluorophenylsulfur trifluoride, each isomer of bromofluorophenylsulfur trifluoride, each isomer of tolylsulfur trifluoride, each isomer of chloro(methyl)phenylsulfur trifluoride, each isomer of dimethylphenylsulfur trifluoride, each isomer of chloro(dimethyl)phenylsulfur trifluoride, each isomer of trimethylphenylsulfur trifluoride, each isomer of ethylphenylsulfur trifluoride, each isomer of propylphenylsulfur trifluoride, each isomer of butylphenylsulfur trifluoride, each isomer of nitrophenylsulfur trifluoride, each isomer of dinitrophenylsulfur trifluoride, and so on.

As mentioned in the reaction mechanism for the Process I, arylsulfur trifluorides (formula V) can be the intermediates in the Process I.

A halogen employable in the present invention for Process III is the same as for Process I described above except for the amount used for the reaction.

Fluoro salts having a formula (III) for Process III are the same as for Process I described above except for the amount used in the reaction.

It is preferable that the reaction of Process III be carried out using a solvent. Examples of suitable solvents are the same as for Process I described above.

In order to economically get good yields of the products, the reaction temperature for Process III can be selected in the range of −60° C.~+70° C. More preferably, the temperature can be selected in the range of −40° C.~+50° C. Furthermore preferably, the temperature can be selected in the range of −20° C.~+40° C.

In order to get good economic yields of product, the amount of a halogen used can be preferably selected in the range of from about 1 to about 5 mol, more preferably from about 1 to about 3 mol, against 1 mol of arylsulfur trifluoride (V).

In order to get good economic yield of the products, the amount of fluoro salt (III) used can be preferably selected in the range of about 1 to about 5 mol against 1 mol of arylsulfur trifluoride (V).

The reaction time for Process III is dependent on reaction temperature, the substrates, reagents, solvents, and their amounts used. Therefore, one can choose the time necessary for completing each reaction based on modification of the above parameters, but can be from about 0.5 h to several days, preferably, within a few days.

Process II is as described above.

Embodiments of the present invention include a process (Process III) which comprises reacting an arylsulfur trifluoride having a formula (V) with a halogen (chlorine, bromine, iodine, or interhalogens) and a fluoro salt having a formula (III) to form an arylsulfur halotetrafluoride having a formula (IV) and (Process II') reacting the obtained arylsulfur halotetrafluoride with a fluoride source in the presence of a halogen selected from the group of chlorine, bromine, iodine, and interhalogens to form the arylsulfur pentafluoride having a formula (I). Scheme 6 showing Processes III and II' are shown as follows:

Scheme 6 (Processes III and II')

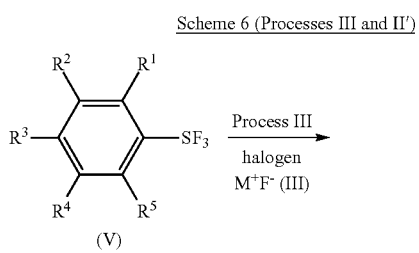

-continued

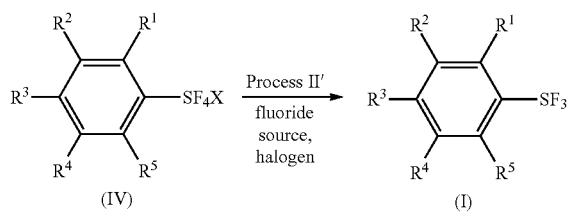

With regard to formulas (I), (III), (IV), and (V), $R^1$, $R^2$, $R^3$, $R^4$, $R^5$, $R^6$, M and X have the same meaning as defined above.

Processes III and II' are as described above.

Furthermore, the present invention includes a process (Scheme 7, Process I) for preparing an arylsulfur halotetrafluoride having a formula (IV), which comprises reacting at least one aryl sulfur compound having a formula (IIa) or a formula (IIb) with a halogen selected from the group of chlorine, bromine, iodine, and interhalogens and a fluoro salt having a formula (III) to form the arylsulfur halotetrafluoride.

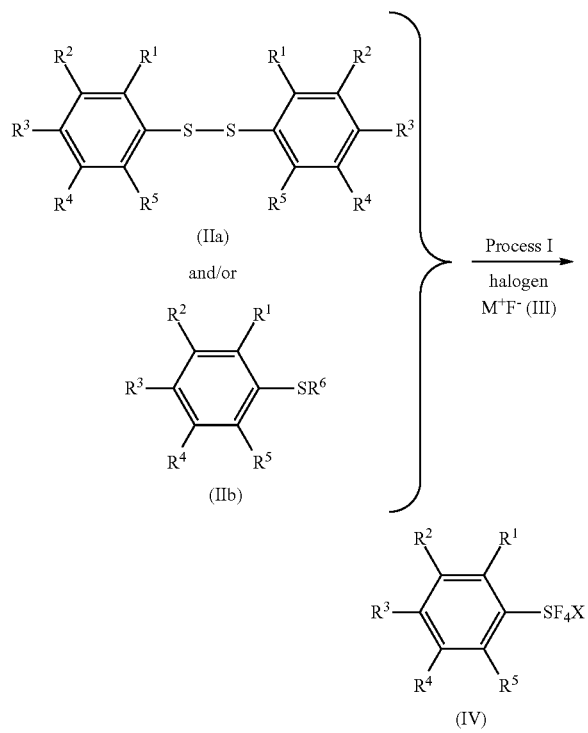

In the formulas (IIa), (IIb), (III), and (IV), $R^1$, $R^2$, $R^3$, $R^4$, $R^5$, $R^6$, M and X represent the same meaning as defined above.

Process I is described above.

Furthermore, the present invention includes a process (Scheme 8, Process III) for preparing an arylsulfur halotetrafluoride having a formula (IV), which comprises reacting an arylsulfur trifluoride having a formula (V) with a halogen selected from the group of chlorine, bromine, iodine, and interhalogens and a fluoro salt having a formula (III) to form the arylsulfur halotetrafluoride.

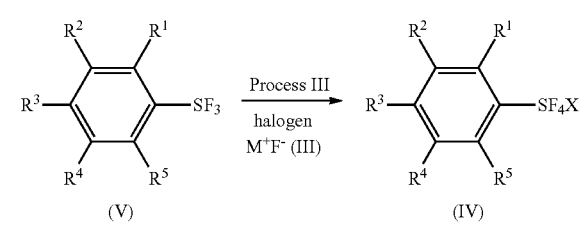

In the formulas (III), (IV), and (V), $R^1$, $R^2$, $R^3$, $R^4$, $R^5$, M and X represent the same meaning as defined above.

Process III is as described above.

Furthermore, the present invention includes a process (Scheme 9, Process II") for preparing an arylsulfur pentafluoride having a formula (I), which comprises reacting an arylsulfur halotetrafluoride having a formula (IV) with a fluoride source whose boiling point is approximately 0° C. or more to form the arylsulfur pentafluoride.

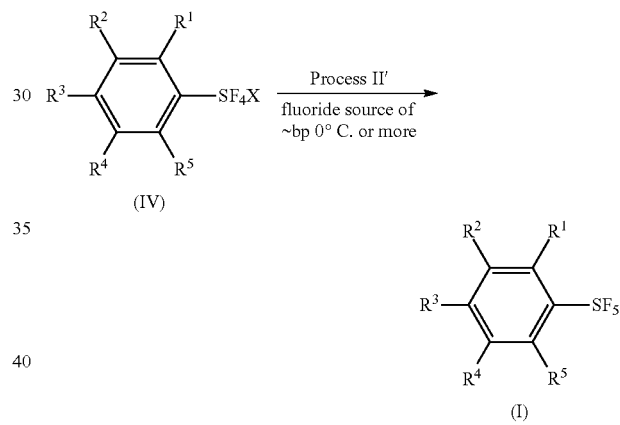

In the formulas (I) and (IV), $R^1$, $R^2$, and X represent the same meaning as defined above.

Process II" (Scheme 9)

Process II" is a reaction of arylsulfur halotetrafluoride having a formula (IV) with a fluoride source whose boiling point is approximately 0° C. or more at 1 atm, as shown in Scheme 9.

The substituent(s), $R^1$, $R^2$, $R^3$, $R^4$, and $R^5$, of the products represented by the formula (I) may be different from the substituent(s), $R^1$, $R^2$, $R^3$, $R^4$, and $R^5$, of the starting materials represented by the formula (IV). Thus, embodiments of this invention include transformation of the $R^1$, $R^3$, $R^4$, and $R^5$ to different $R^1$, $R^2$, $R^3$, $R^4$, and $R^5$ which may take place during the reaction of the present invention or under the reaction conditions as long as the —$SF_4X$ is transformed to a —$SF_5$ group.

Process II" is the same as Process II described above, and, the fluoride sources employable in Process II" are the same as the fluoride sources previously discussed with reference to Process II, with exception that Process II" fluoride sources have boiling points equal to or above 0° C. at 1 atm.

Furthermore, the present invention includes a process (Scheme 10, Process II') for preparing an arylsulfur pentafluoride having a formula (I), which comprises reacting an arylsulfur halotetrafluoride having a formula (IV) with a fluoride source in the presence of a halogen selected from the group of chlorine, bromine, iodine, and interhalogens to form the aryl sulfurpentafluoride.

Scheme 10 (Process II')

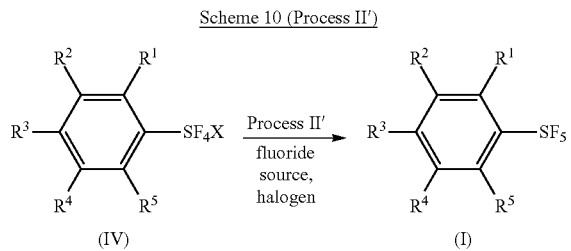

For formulas (I) and (IV), $R^1$, $R^2$, $R^3$, $R^4$, $R^5$, and X represent the same meaning as defined above.

Process II' is as described above.

According to the present invention, the arylsulfur pentafluorides having the formula (I) can be easily and cost-effectively produced from easily available starting materials.

The present invention provides novel arylsulfur chlorotetrafluorides represented by formula (IV') as useful intermediates;

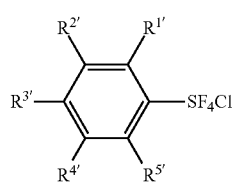

(IV')

wherein $R^{1'}$, $R^{2'}$, $R^{3'}$, $R^{4'}$, and $R^{5'}$ each is independently a hydrogen atom, a halogen atom, a linear or branched alkyl group having one to four carbon atoms, or a nitro group; and where, when $R^{3'}$ is a hydrogen atom, a methyl group, or a nitro group, at least one of $R^{1'}$, $R^{2'}$, $R^{4'}$, and $R^{5'}$ is a halogen atom, a linear or branched alkyl group having one to four carbon atoms, or a nitro group. The halogen atom here is a fluorine atom, a chlorine atom, a bromine atom, or an iodine atom.

Among these, each isomer of tert-butylphenylsulfur chlorotetrafluoride, each isomer of fluorophenylsulfur chlorotetrafluoride, each isomer of chlorophenylsulfur chlorotetrafluoride, each isomer of bromophenylsulfur chlorotetrafluoride, each isomer of difluorophenylsulfur chlorotetrafluoride, each isomer of trifluorophenylsulfur chlorotetrafluoride, and 2,3,4,5,6-pentafluorophenylsulfur chlorotetrafluoride are preferable, and 4-tert-butylphenylsulfur chlorotetrafluoride, 4-fluorophenylsulfur chlorotetrafluoride, 2-fluorophenylsulfur chlorotetrafluoride, 4-chlorophenylsulfur chlorotetrafluoride, 4-bromophenylsulfur chlorotetrafluoride, 3-bromophenylsulfur chlorotetrafluoride, 2,6-difluorophenylsulfur chlorotetrafluoride, 2,4,6-trifluorophenylsulfur chlorotetrafluoride, and 2,3,4,5,6-pentafluorophenylsulfur chlorotetrafluoride are more preferable.

The present invention also provides novel and useful fluorinated arylsulfur pentafluorides represented by formula (I');

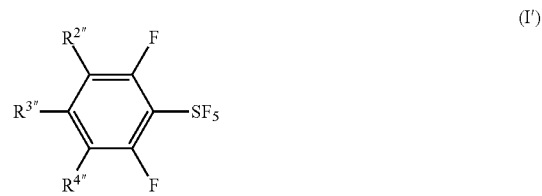

(I')

wherein at least one of $R^{2''}$, $R^{3''}$, and $R^{4''}$ are a halogen atom and the remainders are a hydrogen atom. The halogen atom here is a fluorine atom, a chlorine atom, a bromine atom, or an iodine atom.

Among these, 2,3,4,5,6-pentafluorophenylsulfur pentafluoride, 2,4,6-trifluorophenylsulfur pentafluoride, 3-chloro-2,4,6-trifluorophenylsulfur pentafluoride, and 3-chloro-2,6-difluorophenylsulfur pentafluoride are preferable.

The following examples will illustrate the present invention in more detail, but it should be understood that the present invention is not deemed to be limited thereto.

EXAMPLES

The following examples are provided for illustrative purposes only and are not intended to limit the scope of the invention. Table 2 provides structure names and formulas for reference when reviewing the following examples:

TABLE 2

Arylsulfur Halotetrafluorides (Formula Ia,b,d-n and IVa-j,l,n):

| Formula Number | Name | Structure |
|---|---|---|
| Ia | Phenylsulfur pentafluoride | ⟨phenyl⟩—SF₅ |
| Ib | p-Methylphenylsulfur pentafluoride | CH₃—⟨phenyl⟩—SF₅ |
| Id | p-Fluorophenylsulfur pentafluoride | F—⟨phenyl⟩—SF₅ |
| Ie | o-Fluorophenylsulfur pentafluoride | ⟨phenyl with o-F⟩—SF₅ |
| If | p-Chlorophenylsulfur pentafluoride | Cl—⟨phenyl⟩—SF₅ |
| Ig | p-Bromophenylsulfur pentafluoride | Br—⟨phenyl⟩—SF₅ |
| Ih | m-Bromophenylsulfur pentafluoride | ⟨phenyl with m-Br⟩—SF₅ |

TABLE 2-continued

Arylsulfur Halotetrafluorides (Formula Ia,b,d-n and IVa-j,l,n):

| Formula Number | Name | Structure |
|---|---|---|
| Ii | p-Nitrophenylsulfur pentafluoride | $O_2N$—C$_6$H$_4$—$SF_5$ |
| Ij | 2,6-Difluorophenylsulfur pentafluoride | 2,6-F$_2$C$_6$H$_3$—$SF_5$ |
| Ik | 3-Chloro-2,6-difluorophenylsulfur pentafluoride | 3-Cl-2,6-F$_2$C$_6$H$_2$—$SF_5$ |
| Il | 2,4,6-Trifluorophenylsulfur pentafluoride | 2,4,6-F$_3$C$_6$H$_2$—$SF_5$ |
| Im | 3-Chloro-2,4,6-trifluorophenylsulfur pentafluoride | 3-Cl-2,4,6-F$_3$C$_6$H—$SF_5$ |
| In | 2,3,4,5,6-Pentafluorophenylsulfur pentafluoride | C$_6$F$_5$—$SF_5$ |
| IVa | Phenylsulfur chlorotetrafluoride | C$_6$H$_5$—$SF_4Cl$ |
| IVb | p-Methylphenylsulfur chlorotetrafluoride | $CH_3$—C$_6$H$_4$—$SF_4Cl$ |
| IVc | p-(tert-Butyl)phenylsulfur chlorotetrafluoride | (t-Bu)—C$_6$H$_4$—$SF_4Cl$ |
| IVd | p-Fluorophenylsulfur chlorotetrafluoride | F—C$_6$H$_4$—$SF_4Cl$ |
| IVe | o-Fluorophenylsulfur chlorotetrafluoride | 2-F-C$_6$H$_4$—$SF_4Cl$ |
| IVf | p-Chlorophenylsulfur chlorotetrafluoride | Cl—C$_6$H$_4$—$SF_4Cl$ |
| IVg | p-Bromophenylsulfur chlorotetrafluoride | Br—C$_6$H$_4$—$SF_4Cl$ |
| IVh | m-Bromophenylsulfur chlorotetrafluoride | 3-Br-C$_6$H$_4$—$SF_4Cl$ |
| IVi | p-Nitrophenylsulfur chlorotetrafluoride | $O_2N$—C$_6$H$_4$—$SF_4Cl$ |
| IVj | 2,6-Difluorophenylsulfur chlorotetrafluoride | 2,6-F$_2$C$_6$H$_3$—$SF_4Cl$ |
| IVl | 2,4,6-Trifluorophenylsulfur chlorotetrafluoride | 2,4,6-F$_3$C$_6$H$_2$—$SF_4Cl$ |
| IVn | 2,3,4,5,6-Pentafluorophenylsulfur chlorotetrafluoride | C$_6$F$_5$—$SF_4Cl$ |

Example 1

Synthesis of Phenylsulfur Pentafluoride from Diphenyl Disulfide $$C_6H_5\text{—S—S—}C_6H_5 \xrightarrow[KF]{Cl_2} \text{Process I}$$

-continued

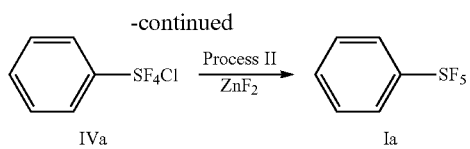

(Process I) A 500 mL round bottom glassware flask was charged with diphenyl disulfide (33.0 g, 0.15 mol), dry KF (140 g, 2.4 mol) and 300 mL of dry $CH_3CN$. The stirred reaction mixture was cooled on an ice/water bath under a flow of $N_2$ (18 mL/min) After $N_2$ was stopped, chlorine ($Cl_2$) was bubbled into a reaction mixture at the rate of about 70 mL/min. The $Cl_2$ bubbling took about 6.5 h. The total amount of $Cl_2$ used was about 1.2 mol. After $Cl_2$ was stopped, the reaction mixture was stirred for additional 3 h. $N_2$ was then bubbled through for 2 hours to remove an excess of $Cl_2$. The reaction mixture was then filtered with 100 mL of dry hexanes in air. About 1 g of dry KF was added to the filtrate. The KF restrains possible decomposition of the product. The filtrate was evaporated under vacuum and the resulting residue was distilled at reduced pressure to give a colorless liquid (58.0 g, 88%) of phenylsulfur chlorotetrafluoride: b.p. 80° C./20 mmHg; $^1H$ NMR ($CD_3CN$) 7.79-7.75 (m, 2H, aromatic), 7.53-7.49 (m, 3H, aromatic); $^{19}F$ NMR ($CD_3CN$) 136.7 (s, $SF_4Cl$). The NMR analysis showed phenylsulfur chlorotetrafluoride obtained is a trans isomer.

(Process II) A 100 mL fluoropolymer (TEFLON®PFA) vessel was charged with $PhSF_4Cl$ (44 g, 0.2 mol) and dry $ZnF_2$ (12.3 g, 0.12 mol) in a dry box filled with $N_2$. The vessel was then equipped with a condenser made of fluoropolymer and a balloon filled with $N_2$. The reaction mixture was slowly heated to 120° C. over a period of one hour. The reaction mixture changed from colorless to yellow, pink, and then eventually green. The reaction mixture was stirred at 120° C. for 20 h. After being cooled to room temperature, about 50 mL of pentane was added to the reaction mixture. The mixture was filtered to remove all insoluble solid to give a yellow solution, which was concentrated. The resulting residue was distilled at reduced pressure to give 30.6 g (75%) of phenylsulfur pentafluoride; b.p. 70-71° C./120 mmHg; $^1H$ NMR ($CDCl_3$) 7.77-7.74 (m, 2H, aromatic), 7.60-7.40 (m, 3H, aromatic); $^{19}F$ NMR ($CDCl_3$) δ5.20-84.13 (m, 1F, $SF_5$), 62.91 (d, 4F, $SF_5$).

Examples 2-10

Synthesis of Arylsulfur Pentafluorides (I) from Aryl Sulfur Compounds (IIa)

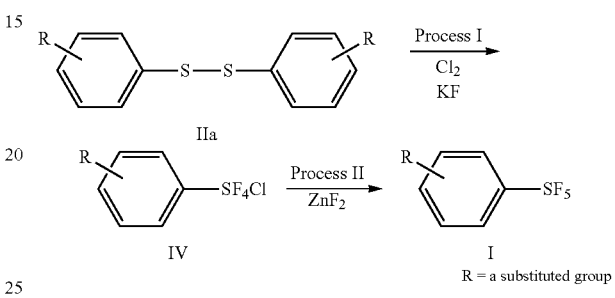

R = a substituted group

Substituted arylsulfur pentafluorides (I) were synthesized from the corresponding aryl sulfur compounds (IIa) by the similar procedure as in Example 1. Table 3 shows the synthesis of the substituted arylsulfur pentafluorides. Table 3 also shows the starting materials and other chemicals necessary for the Processes I and II, solvents, reaction conditions, and the results, together with those of Example 1. FC-72 (Fluorinert®) was used as a solvent in Process II in Examples 9 and 10. The Fluorinert® FC-72 was a perfluorinated organic compound having a boiling point of 56° C., which was a product made by 3M Company.

TABLE 3

Production of Arylsulfur pentafluorides (I) from Aryl sulfur compounds (IIa)

| Ex. | (IIa) | Halogen | (III) | Solvent | Conditions | (IV) | Yield |
|---|---|---|---|---|---|---|---|
| 1 | 33.0 g (0.15 mol) | $Cl_2$ ~1.2 mol | KF 140 g (2.4 mol) | $CH_3CN$ 300 mL | 0~5° C. ~9.5 h | IVa 58 g | 88% |
| 2 | 123 g (05 mol) | $Cl_2$ 0.73 mol | KF 464 g (8 mol) | $CH_3CN$ 1 L | 0° C. 10.5 h | IVb 170 g | 73% |
| 3 | 10.0 g (0.039 mol) | $Cl_2$ 0.28 mol | KF 36 g (0.63 mol) | $CH_3CN$ 100 mL | 0~5° C. 2.5 h and r.t. overnight | IVd 12.5 g | 67% |

TABLE 3-continued

| | Substrate | Reagent | Fluoride | Solvent | Conditions | Product | Yield |
|---|---|---|---|---|---|---|---|
| 4 | (2-F-C₆H₄-S)₂<br>10.0 g<br>(0.039 mol) | Cl₂<br>0.31 mol | KF<br>36.5 g<br>(0.63 mol) | CH₃CN<br>100 mL | 0~5° C.<br>1.8 h<br>and r.t.<br>overnight | 2-F-C₆H₄-SF₄Cl<br>IVe<br>14.9 g | 80% |
| 5 | (4-Br-C₆H₄-S)₂<br>37.6 g<br>(0.1 mol) | Cl₂<br>0.72 mol | KF<br>94 g<br>(1.6 mol) | CH₃CN<br>200 mL | 0~5° C.<br>4.5 h<br>and r.t.<br>overnight | 4-Br-C₆H₄-SF₄Cl<br>IVg<br>46.2 g | 77% |
| 6 | (3-Br-C₆H₄-S)₂<br>47.7 g<br>(0.127 mol) | Cl₂<br>0.88 mol | KF<br>118 g<br>(2.0 mol) | CH₃CN<br>250 mL | 0~5° C.<br>5.5 h<br>and r.t.<br>overnight | 3-Br-C₆H₄-SF₄Cl<br>IVh<br>65.7 g | 86% |
| 7 | (4-O₂N-C₆H₄-S)₂<br>30.8 g<br>(0.1 mol) | Cl₂<br>0.72 mol | KF<br>94 g<br>(1.6 mol) | CH₃CN<br>200 mL | 0~5° C.<br>4.5 h<br>and r.t.<br>overnight | 4-O₂N-C₆H₄-SF₄Cl<br>IVi<br>32 g | 60% |
| 8 | (2,6-F₂-C₆H₃-S)₂<br>29.1 g<br>(0.1 mol) | Cl₂<br>~1.02 mol | CsF<br>279 g<br>(1.83 mol) | CH₃CN<br>200 mL | 0~5° C.<br>5 h<br>and r.t.<br>overnight | 2,6-F₂-C₆H₃-SF₄Cl<br>IVj<br>42.3 g | 82% |
| 9 | (2,4,6-F₃-C₆H₂-S)₂<br>22.9 g<br>(0.07 mol) | Cl₂<br>~1.08 mol | KF<br>90 g<br>(1.55 mol) | CH₃CN<br>300 mL | 0~5° C.<br>6 h<br>and r.t.<br>overnight | 2,4,6-F₃-C₆H₂-SF₄Cl<br>IVl<br>25.8 g | 67% |
| 10 | (C₆F₅-S)₂<br>26.1 g<br>(0.065 mol) | Cl₂<br>~1 mol | KF<br>82 g<br>(1.41 mol) | CH₃CN<br>300 mL | 0~5° C.<br>5 h<br>and r.t.<br>overnight | C₆F₅-SF₄Cl<br>IVn<br>34.9 g | 86% |

TABLE 3-continued

|  |  | Process II | | | | |
|---|---|---|---|---|---|---|
| Ex. | Amount of (IV) | Fluoride source | Solv. | Conditions | (I) | Yield |
| 1 | 44 g (0.2 mol) | ZnF₂ 12.3 g (0.12 mol) | non | 120° C. 20 h | 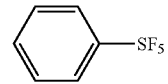<br>Ia<br>30.6 g | 75% |
| 2 | 32 g (137 mmol) | ZnF₂ 8.47 g (82 mmol) | non | 90° C. overnight | 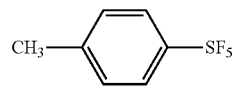<br>Ib<br>21.1 g | 71% |
| 3 | 10 g (42 mmol) | ZnF₂ 2.6 g (25 mmol) | non | 120° C. 16 h | 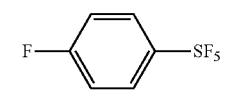<br>Id<br>5.8 g | 62% |
| 4 | 10 g (42 mmol) | ZnF₂ 2.59 g (25 mmol) | non | 120 °C. 15 h | 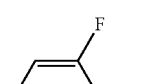<br>Ie<br>22.3 g | 59% |
| 5 | 30 g (100 mmol) | ZnF₂ 6.18 g (60 mmol) | heptane 20 mL | reflux 17 h | 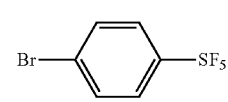<br>Ig<br>22.3 g | 79% |
| 6 | 10 g (33 mmol) | ZnF₂ 2.0 g (20 mmol) | non | 120° C. 15 h | 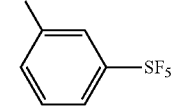<br>Ih<br>6.8 g | 78% |
| 7 | 26.5 g (100 mmol) | ZnF₂ 6.18 g (60 mmol) | non | 150° C. 72 h | 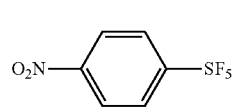<br>Ii<br>9.0 g | 36% |
| 8 | 41.87 g (0.16 mol) | ZnF₂ 18.1 g (0.17 mol) | non | 130° C. 4 h and 180 C. 6 h | 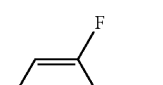<br>Ij<br>20.0 g | 52% |

TABLE 3-continued

| | | | | | | |
|---|---|---|---|---|---|---|
| 9 | 4.09 g (14.9 mmol) | SbF$_5$ 0.5~0.6 mL (~8 mmol) | FC-72 20 mL | r.t. 2 h | 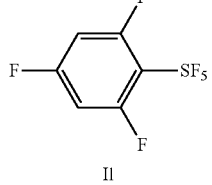<br>Il<br><br>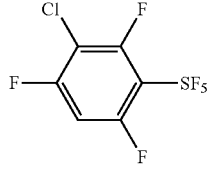<br>Im<br>3.19 g (total) | 60%<br><br><br>20% |
| 10 | 9.47 g (30.5 mmol) | SbF$_5$ 3.41 g (30.5 mmol) | FC-72 40 mL | r.t. 2 h | 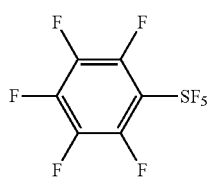<br>In<br>5.36 g | 60% |

The properties and spectral data of the products, (IV) and (I), obtained by Examples 2-10 are shown by the following:

p-Methylphenylsulfur chlorotetrafluoride; b.p. 74-75° C./5 mmHg; $^1$H NMR (CD$_3$CN) 7.65 (d, 2H, aromatic), 7.29 (d, 2H, aromatic), 2.36 (s, 3H, CH$_3$); $^{19}$F NMR (CD$_3$CN) 137.66 (s, SF$_4$Cl); High resolution mass spectrum; found 235.986234 (34.9%) (calcd for C$_7$H$_7$F$_4$S$^{37}$Cl; 235.986363). found 233.989763 (75.6%) (calcd for C$_7$H$_7$F$_4$S$^{35}$Cl; 233.989313). The NMR shows that p-methylphenylsulfur chlorotetrafluoride obtained is a trans isomer.

p-Methylphenylsulfur pentafluoride; b.p. 95-96° C./80 mmHg; $^1$H NMR (CDCl$_3$) 7.63 (d, 2H, aromatic), 7.24 (d, 2H, aromatic), 2.40 (s, 3H, CH$_3$); $^{19}$F NMR (CDCl$_3$) δ6.55-84.96 (m, 1F, SF), 63.26 (d, 4F, SF$_4$).

p-Fluorophenylsulfur chlorotetrafluoride; b.p. 60° C./8 mmHg; $^1$H NMR (CD$_3$CN) 7.85-7.78 (m, 2H, aromatic), 7.25-7.15 (m, 2H, aromatic); $^{19}$F NMR (CD$_3$CN) 137.6 (s, SF$_4$Cl), -108.3 (s, CF); High resolution mass spectrum; found 239.961355 (37.4%) (calcd for C$_6$H$_4$F$_5$S$^{37}$Cl; 239.961291). found 237.964201 (100%) (calcd for C$_6$H$_4$F$_5$S$^{35}$Cl; 237.964241). The NMR shows that p-fluorophenylsulfur chlorotetrafluoride obtained is a trans isomer.

p-Fluorophenylsulfur pentafluoride; b.p. 71° C./80 mmHg; $^1$H NMR (CDCl$_3$) 7.80-7.73 (m, 2H, aromatic), 7.17-7.09 (m, 2H, aromatic); $^{19}$F NMR (CDCl$_3$) δ7.78-83.17 (m, 1F, SF), 63.81 (d, 4F, SF$_4$), -107.06 (s, 1F, CF); GC-MS m/z 222 (M$^+$).

o-Fluorophenylsulfur chlorotetrafluoride; b.p. 96-97° C./20 mmHg; $^1$H NMR (CD$_3$CN) 7.77-7.72 (m, 1H, aromatic), 7.60-7.40 (m, 1H, aromatic), 7.25-7.10 (m, 2H, aromatic); $^{19}$F NMR (CD$_3$CN) 140.9 (d, SF$_4$Cl), -107.6 (s, CF); High resolution mass spectrum; found 239.961474 (25.4%) (calcd for C$_6$H$_4$F$_5$S$^{37}$Cl; 239.961291). found 237.964375 (69.8%) (calcd for C$_6$H$_4$F$_5$S$^{35}$Cl; 237.964241). The NMR shows that o-fluorophenylsulfur chlorotetrafluoride obtained is a trans isomer.

o-Fluorophenylsulfur pentafluoride; b.p. 91-94° C./120 mmHg; $^1$H NMR (CDCl$_3$) 7.78-7.73 (m, 1H, aromatic), 7.55-7.48 (m, 1H, aromatic), 7.27-7.17 (m, 2H, aromatic); $^{19}$F NMR (CDCl$_3$) δ2.38-81.00 (m, 1F, SF), 68.10 (dd, 4F, SF$_4$), -108.07-(-108.35) (m, 1F, CF).

p-Bromophenylsulfur chlorotetrafluoride (X); m.p. 58-59° C.; $^1$H NMR (CD$_3$CN) δ 7.67 (s, 4H, aromatic); $^{19}$F NMR (CD$_3$CN) δ 136.56 (s, SF$_4$Cl); High resolution mass spectrum; found 301.877066 (16.5%) (calcd for C$_6$H$_4$$^{81}$Br$^{37}$ClF$_4$S; 301.879178). found 299.880655 (76.6%) (calcd for C$_6$H$_4$$^{81}$Br$^{35}$ClF$_4$S; 299.881224 and calcd for C$_6$H$_4$$^{79}$Br$^{37}$ClF$_4$S; 299.882128). found 297.882761 (77.4%) (calcd for C$_6$H$_4$$^{79}$Br$^{35}$ClF$_4$S; 297.884174). Elemental analysis; calcd for C$_6$H$_4$BrClF$_4$S; C, 24.06%; H, 1.35%; found, C, 24.37%; H, 1.54%. The NMR showed that p-bromophenylsulfur chlorotetrafluoride was obtained as a trans isomer.

p-Bromophenylsulfur pentafluoride; b.p. 77-78° C./10 mmHg; $^1$H NMR (CDCl$_3$) 7.63 (s, 4H, aromatic); $^{19}$F NMR (CDCl$_3$) δ4.13-82.53 (m, 1F, SF), 63.11 (d, 4F, SF$_4$).

m-Bromophenylsulfur chlorotetrafluoride; b.p. 57-59° C./0.8 mmHg; $^1$H NMR (CD$_3$CN) 7.90-7.88 (m, 1H, aromatic), 7.70-7.50 (m, 2H, aromatic), 7.40-7.30 (m, 1H, aromatic); $^{19}$F NMR (CD$_3$CN) 136.74 (s, SF$_4$Cl). High resolution mass spectrum; found 301.878031 (29.1%) (calcd for C$_6$H$_4$$^{81}$Br$^{37}$ClF$_4$S; 301.879178). found 299.881066 (100%) (calcd for C$_6$H$_4$$^{81}$Br$^{35}$ClF$_4$S; 299.881224 and calcd for C$_6$H$_4$$^{79}$Br$^{37}$ClF$_4$S; 299.882128), found 297.883275 (77.4%) (calcd for C$_6$H$_4$$^{79}$Br$^{35}$ClF$_4$S; 297.884174). The NMR showed that m-bromophenylsulfur chlorotetrafluoride obtained was a trans isomer.

m-Bromophenylsulfur pentafluoride; b.p. 69-70° C./10 mmHg; $^1$H NMR (CDCl$_3$) 7.91 (t, 1H, aromatic), 7.72-7.64 (m, 2H, aromatic), 7.35 (t, 1H, aromatic); $^{19}$F NMR (CDCl$_3$) δ3.55-82.47 (m, 1F, SF), 63.13 (d, 4F, SF$_4$).

p-Nitrophenylsulfur chlorotetrafluoride; m.p. 130-131° C.; $^1$H NMR (CD$_3$CN) 8.29 (d, J=7.8 Hz, 2H, aromatic), 8.02

(d, J=7.8 Hz, 2H, aromatic); $^{19}$F NMR (CD$_3$CN) 134.96 (s, SF$_4$Cl); High resolution mass spectrum; found 266.956490 (38.4%) (calcd for C$_6$H$_4$$^{37}$ClF$_4$NO$_2$S; 266.955791). found 264.959223 (100%) (calcd for C$_6$H$_4$$^{35}$ClF$_4$NO$_2$S; 264.958741). Elemental analysis; calcd for C$_6$H$_4$ClF$_4$NO$_2$S; C, 27.13%; H, 1.52%; N, 5.27%; found, C, 27.16%; H, 1.74%; N, 4.91%. The NMR shows that p-nitrophenylsulfur chlorotetrafluoride obtained is a trans isomer.

p-Nitrophenylsulfur pentafluoride; b.p. 74-76° C./3 mmHg; $^1$H NMR (CDCl$_3$) 8.36-8.30 (m, 2H, aromatic), 7.99-7.95 (m, 2H, aromatic); $^{19}$F NMR (CDCl$_3$) δ2.32-80.69 (m, 1F, SF), 62.76 (d, 4F, SF$_4$).

2,6-Difluorophenylsulfur chlorotetrafluoride: The product (b.p. 120-122° C./95-100 mmHg) obtained from Example 8 is a 6:1 mixture of trans- and cis-isomers of 2,6-difluorophenylsulfur chlorotetrafluoride. The trans-isomer was isolated as pure form by crystallization; mp. 47.6-48.3° C.; $^{19}$F NMR (CDCl$_3$) δ 143.9 (t, J=26.0 Hz, 4F, SF$_4$), -104.1 (quintet, J=26.0 Hz, 2F, 2,6-F): $^1$H NMR (CDCl$_3$) δ 6.97-7.09 (m, 2H, 3,5-H), 7.43-7.55 (m, 1H, 4-H); $^{13}$C NMR (CDCl$_3$) δ 157.20 (d, J=262.3 Hz), 133.74 (t, J=11.6 Hz), 130.60 (m), 113.46 (d, J=14.6 Hz); high resolution mass spectrum; found 257.950876 (37.6%) (calcd for C$_6$H$_3$$^{37}$ClF$_6$S; 257.951869). found 255.955740 (100%) (calcd for C$_6$H$_3$$^{35}$ClF$_6$S; 255.954819); elemental analysis; calcd for C$_6$H$_3$ClF$_6$S; C, 28.08%, H, 1.18%; found; C, 28.24%, H, 1.24%. The cis-isomer was assigned in the following; $^{19}$F NMR (CDCl$_3$) δ 158.2 (quartet, J=161.8 Hz, 1F, SF), 121.9 (m, 2F, SF$_2$), 76.0 (m, 1F, SF). The $^{19}$F NMR assignment of aromatic fluorine atoms of the cis-isomer could not be done because of possible overlapping of the peaks of the trans-isomer.

2,6-Difluorophenylsulfur pentafluoride: m.p. 40.3-41.1° C.; $^1$H NMR (CDCl$_3$) δ 7.51 (m, 1H), 7.04 (m, 2H); $^{19}$F NMR (CDCl$_3$) δ2.32-80.69 (m, 1F, SF), 62.76 (d, 4F, SF$_4$); high resolution mass spectrum; found 239.984509 (calcd for C$_6$H$_3$F$_7$S; 239.984370); elemental analysis, calcd for C$_6$H$_3$F$_7$S; C, 30.01%, H, 1.26%; found, C, 30.20%, H, 1.47%.

2,4,6-Trifluorophenylsulfur chlorotetrafluoride: trans-isomer; m.p. 55.8-56.7° C.; $^{19}$F NMR (CDCl$_3$) δ 144.07 (t, J=26.0 Hz, 4F, SF$_4$), -99.80 (t, J=26.0 Hz, 2F, o-F), -100.35 (s, 1F, p-F); $^1$H NMR (CDCl$_3$) δ 6.79 (t, J=17.5 Hz, m-H); $^{13}$C NMR (CDCl$_3$) δ 164.16 (dt, J=164.2 Hz, 15.2 Hz, 4-C), 158.18 (dm, J=260.7 Hz, 2-C), 127.7 (m, 1-C), 102.1 (tm, J=27.8 Hz, 3-C). Elemental analysis; calcd for C$_6$H$_2$ClF$_7$S; C, 26.24%; H, 0.73%; found, C, 26.23%; H, 1.01%. The NMR shows that 2,4,6-trifluorophenylsulfur chlorotetrafluoride obtained is a trans isomer.

2,4,6-Trifluorophenylsulfur pentafluoride and 3-chloro-2,4,6-trifluorophenylsulfur pentafluoride: The product (b.p.~145° C.) obtained from Experiment 9 was a 3:1 (molar ratio) mixture of 2,4,6-trifluorophenylsulfur pentafluoride and 3-chloro-2,4,6-trifluorophenylsulfur pentafluoride. These products were identified by NMR and GC-Mass analysis. 2,4,6-Trifluorophenylsulfur pentafluoride: $^{19}$F NMR (CDCl$_3$) δ 78.7-75.3 (m, SF), 73.8-72.9 (m, SF$_4$), -100.6 (m, 4-F), -100.7 (m, 2,6-F); $^1$H NMR (CDCl$_3$) δ 6.80 (t, J=8.6 Hz, 3,5-H); GC-Mass m/z 258 (M$^+$). 3-Chloro-2,4,6-trifluorophenylsulfur pentafluoride: $^{19}$F NMR (CDCl$_3$) δ 78.7-75.3 (m, SF), 73.8-72.9 (m, SF$_4$), -101.3 (m, 2 or 6-F), -102.3 (m, 4-F), -102.6 (m, 2 or 6-F); $^1$H NMR (CDCl$_3$) δ 6.95 (br. t, J=9.5 Hz, 5-H); GC-Mass m/z 294, 292 (M$^+$).

2,3,4,5,6-Pentafluorophenylsulfur chlorotetrafluoride: The product (b.p. 95-112° C./100 mmHg) obtained from Experiment 10 was a 1.7:1 mixture of trans and cis isomers of 2,3,4,5,6-pentafluorophenylsulfur chlorotetrafluoride. The isomers were assigned by $^{19}$F NMR: The trans isomer; $^{19}$F NMR (CDCl$_3$) δ 144.10 (t, J=26.0 Hz, 4F, SF$_4$), -132.7 (m, 2F, 2,6-F), -146.6 (m, 1F, 4-F), -158.9 (m, 2F, 3,5-F); $^{13}$C NMR (CDCl$_3$) δ 143.5 (dm, J=265.2 Hz), 141.7 (dm, J=263.7 Hz), 128.3 (m). The cis isomer; $^{19}$F NMR (CDCl$_3$) δ 152.39 (quartet, J=158.9 Hz, 1F, SF), 124.32 (m, 2F, SF$_2$), 79.4 (m, 1F, SF), -132.7 (m, 2F, 2,6-F), -146.6 (m, 1F, 4-F), -158.9 (m, 2F, 3,5-F). High resolution mass spectrum of a 1.7:1 mixture of the trans and cis isomers; found 311.923124 (15.5%) (calcd for C$_6$$^{37}$ClF$_9$S; 311.923604). found 309.926404 (43.1%) (calcd for C$_6$$^{35}$ClF$_9$S; 309.926554).

2,3,4,5,6-Pentafluorophenylsulfur pentafluoride: b.p. 135-137° C.; $^{19}$F NMR (CDCl$_3$) δ 74.8 (m, 5F, SF$_5$), -133.4 (m, 2F, 2,6-F), -146.2 (m, 1F, 4-F), -158.6 (m, 2F, 3,5-F); $^{13}$C NMR (CDCl$_3$) δ 143.6 (dm, J=262.2 Hz), 137.9 (dm, J=253.6 Hz), 126.7 (m). High resolution mass spectrum; found 293.956492 (calcd for C$_6$F$_{10}$S; 293.956104).

Example 11

Synthesis of Phenylsulfur Pentafluoride from Diphenyl Disulfide with a Mixture of Hydrogen Fluoride and Pyridine as a Fluoride Source in Process II

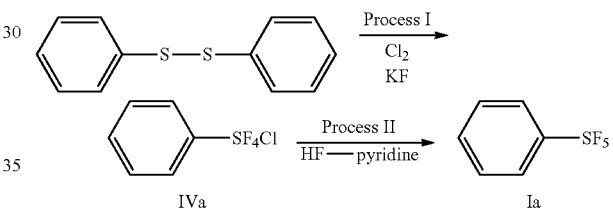

(Process I) Phenylsulfur chlorotetrafluoride was prepared in a high yield in the same manner as in Process I in Example 1.

(Process II) A reaction vessel made of fluoropolymer was charged with 341 mg (1.54 mmol) of trans-phenylsulfur chlorotetrafluoride, and 0.5 mL of a mixture of about 70 wt % hydrogen fluoride and about 30 wt % pyridine was added at room temperature. The reaction mixture was stirred at room temperature for 1 hour and heated at 50° C. for 3 hours. After the reaction, the reaction mixture was cooled to room temperature. An analysis of the reaction mixture by $^{19}$F-NMR showed that phenylsulfur pentafluoride was produced in 93% yield.

Example 12

Synthesis of Phenylsulfur Pentafluoride from Thiophenol as an Aryl Sulfur Compound of Formula (IIb)

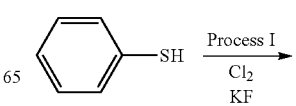

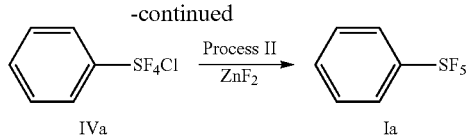

(Process I) Chlorine (Cl$_2$) was passed with a flow rate of 27 mL/min into a stirred mixture of 10.0 g (90.8 mmol) of thiophenol and 47.5 g (0.817 mol) of dry KF in 100 mL of dry acetonitrile at 6~10° C. Chlorine was passed for 3.7 h and the total amount of chlorine passed was 10.2 L (0.445 mol). After 10 mL of 1,1,2-trichlorotrifluoroethane was added to the reaction mixture, the reaction mixture was filtered. After removal of the solvent in vacuum, phenylsulfur chlorotetrafluoride (16.6 g, 83%) as a light green-brown liquid was obtained. The physical properties and spectral data of the product are shown in Example 1. The product was a trans isomer.

(Process II) Phenylsulfur chlorotetrafluoride obtained in Process I above may be allowed to react with ZnF$_2$ in the same procedure as Process II in Example 1, giving phenylsulfur pentafluoride in good yield.

Example 13

Synthesis of P-Nitrophenylsulfur Pentafluoride from P-Nitrobenzenesulfenyl Chloride as an Aryl Sulfur Compound of Formula (IIb)

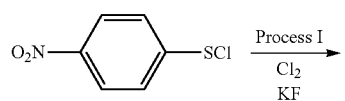

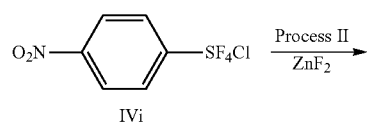

(Process I) Chlorine (Cl$_2$) was passed with a flow rate of 37 mL/min into a stirred mixture of 5.00 g (26.4 mmol) of p-nitrobenzenesulfenyl chloride and 15.3 g (264 mmol) of dry KF in 40 mL of dry acetonitrile at 5~11° C. The total amount of chlorine passed was 2.54 L (113 mmol). After 5 mL of 1,1,2-trichlorotrifluoroethane was added to the reaction mixture, the reaction mixture was filtered. After removal of the solvent in vacuum, p-nitrophenylsulfur chlorotetrafluoride (4.69 g, 76%) as a solid was obtained. The physical properties and spectral data of the product are shown in Example 7. The product was a trans isomer.

(Process II) p-Nitrophenylsulfur chlorotetrafluoride obtained in Process I above may be allowed to react with ZnF$_2$ in the same procedure as Process II in Example 7, giving p-nitrophenylsulfur pentafluoride in good yield.

Example 14

Synthesis of Phenylsulfur Pentafluoride from Phenylsulfur Trifluoride

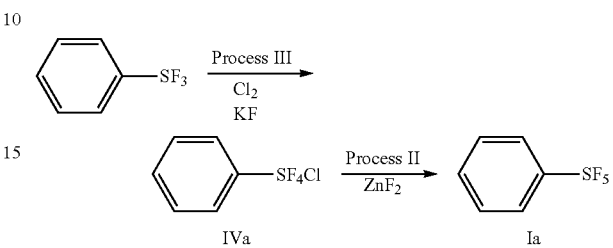

(Process III) Chlorine (Cl$_2$) was passed with a flow rate of 34 mL/min into a stirred mixture of 5.00 g (30.1 mmol) of phenylsulfur trifluoride and 8.74 g (150 mmol) of dry KF in 20 mL of dry acetonitrile at 6~9° C. Chlorine was passed for 43 min and the total amount of chlorine passed was 1.47 L (65.5 mmol). After 3 mL of 1,1,2-trichlorotrifluoroethane was added to the reaction mixture, the reaction mixture was filtered. After removal of the solvent in vacuum, phenylsulfur chlorotetrafluoride (5.62 g, 84%) as a colorless liquid was obtained. The physical properties and spectral data of the product are shown in Example 1. The product was a trans isomer.

(Process II) Phenylsulfur chlorotetrafluoride obtained in Process III above may be allowed to react with ZnF$_2$ in the same procedure as Process II in Example 1, giving phenylsulfur pentafluoride in good yield.

Example 15

Reaction of Phenylsulfur Chlorotetrafluoride and ZnF$_2$ Under a Slow Flow of Chlorine (Presence of Halogen)

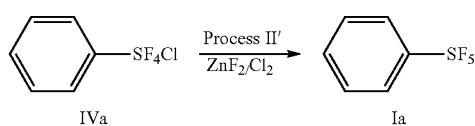

(Process II') trans-Phenylsulfur chlorotetrafluoride (trans-PhSF$_4$Cl) used for this Process was prepared in high yields by the Process I or III as shown by Examples 1, 11, 12, or 14. In a dry box, a 50 mL reaction vessel made of fluoropolymer was charged with 10.0 g (0.045 mol) of trans-PhSF$_4$Cl and 2.8 g (0.027 mol) of dry ZnF$_2$. The reaction vessel was brought out from the dry box and connected to the gas flowing system. The reaction mixture was slowly heated to 120° C. while Cl$_2$ gas was added into the reaction vessel at the rate of 4.6 mL/minute. The progress of the reaction was monitored by $^{19}$F NMR. After 40 minutes at 120° C., three major compounds (trans-PhSF$_4$Cl, cis-PhSF$_4$Cl, and phenylsulfur pentafluoride (PhSF$_5$)) were detected to be present in the reaction mixture. The mol ratio of trans-PhSF$_4$Cl:cis-PhSF$_4$Cl:PhSF$_5$ was 0.5:3.3:100. After additional 60 minutes at 120° C., trans- and cis-PhSF$_4$Cl disappeared and only PhSF$_5$ was detected from $^{19}$F NMR. The reaction was completed within 1.7 h at 120° C. After N$_2$ (5.4 mL/minute) was flowed for 0.5 hour, the examination of the reaction mixture by $^{19}$F NMR using benzotrifluoride as a standard showed that phenylsulfur pentafluoride was produced in 92% yield. This experiment showed that the reaction is greatly accelerated by the presence of chlorine and the product is obtained in a high yield. This experiment also showed that cis-PhSF$_4$Cl is formed intermediately by the isomerization of trans-PhSF$_4$Cl, and cis-PhSF$_4$Cl is converted to the product, PhSF$_5$.

Example 16

Reaction of Phenylslufur Chlorotetrafluoride and ZnF$_2$ Under a Fast Flow of Chlorine (Presence of Halogen)

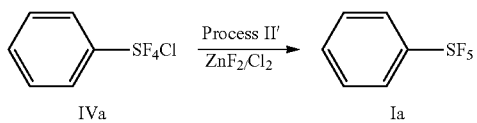

(Process II') trans-Phenylsulfur chlorotetrafluoride (trans-PhSF$_4$Cl) used for this Process was prepared in high yields by the Process I or III as shown by Examples 1, 11, 12 or 14. In a dry box, a 50 mL reaction vessel made of fluoropolymer was charged with 10.0 g (0.045 mol) of trans-PhSF$_4$Cl and 2.8 g (0.027 mol) of dry ZnF$_2$. The reaction vessel was brought out from the dry box and connected to the gas flowing system. The reaction mixture was slowly heated to 120° C. while Cl$_2$ gas was added into the reaction vessel at the rate of 23 mL/minute. The progress of the reaction was monitored by $^{19}$F NMR. After 45 minutes at 120° C., three major compounds (trans-PhSF$_4$Cl, cis-PhSF$_4$Cl, and phenylsulfur pentafluoride (PhSF$_5$)) were detected to be present in the reaction mixture. The mol ratio of trans-PhSF$_4$Cl:cis-PhSF$_4$Cl:PhSF$_5$ was 18:83:100. After additional 45 minutes at 120° C., trans- and cis-PhSF$_4$Cl disappeared and only PhSF$_5$ was detected from $^{19}$F NMR. The reaction was completed in about 1.5 h at 120° C. After N$_2$ (26.9 mL/minute) was flowed for 1 hour, the examination of the reaction mixture by $^{19}$F NMR using benzotrifluoride as a standard showed that phenylsulfur pentafluoride was produced in 83% yield. This experiment showed that the reaction is greatly accelerated by the presence of chlorine and the product is obtained in a high yield. This experiment clearly showed that cis-PhSF$_4$Cl is formed intermediately by the isomerization of trans-PhSF$_4$Cl, and cis-PhSF$_4$Cl is converted to the product, PhSF$_5$.

Example 17

Reaction of 2,6-difluorophenylsulfur Chlorotetrafluoride and ZnF$_2$ Under a Flow of Chlorine (Presence of Halogen)

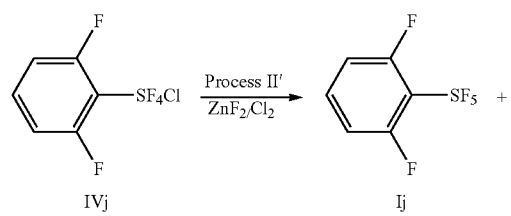

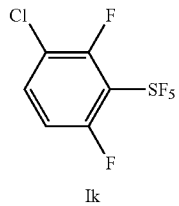

(Process II') A 6:1 mixture of trans and cis-2,6-difluorophenylsulfur chlorotetrafluoride used for this Process was prepared in high yields by the Process I or III as shown by Examples 8. In a dry box, a 100 mL reaction vessel made of fluoropolymer was charged with 13.03 g (0.126 mol) of dry ZnF$_2$ The reaction vessel was brought out from the dry box and connected to the gas flowing system. After nitrogen purge, Cl$_2$ gas started to flow into the reaction vessel at the rate of 15 mL/minute as the reaction vessel was heated to 130-140° C., at which point addition of 32.36 g (0.126 mol) of the mixture of trans- and cis-2,6-difluorophenylsulfur chlorotetrafluoride was started. A total of 32.36 g (0.126 mol) of the mixture of trans- and cis-2,6-difluorophenylsulfur chlorotetrafluoride was added over 1 h. After this, heat and chlorine flow were maintained for an additional 3 hours. At this point, the NMR analysis of the reaction mixture showed that the starting materials (trans- and cis-2,6-difluorophenylsulfur chlorotetrafluoride) were consumed and 2,6-difluorophenylsulfur pentafluoride and 3-chloro-2,6-difluorophenylsulfur pentafluoride were produced in 63:37 molar ratio. The reaction mixture was then extracted with pentane and washed with aqueous sodium carbonate solution. The extract was dried with dry Na$_2$SO$_4$, filtered, and concentrated to give a residue which was distilled at reduced pressure to give four fractions of the product in the range of boiling point 75~120° C. at 110 mmHg. The first three fractions (total 15.37 g) was a 1:1 mixture (by GC) of 2,6-difluorophenylsulfur pentafluoride and 3-chloro-2,6-difluorophenylsulfur pentafluoride. The final fraction (the fourth fraction, b.p. 112-120° C./110 mmHg) had 6.22 g of 3-chloro-2,6-difluorophenylsulfur pentafluoride (93% purity, determined by GC). The spectral data of 3-chloro-2,6-difluorophenylsulfur pentafluoride were as follows; $^{19}$F NMR (CDCl$_3$) δ 77.9-75.7 (m, 1F, SF), 73.2-72.5 (m, 4F, SF$_4$), −103.3 (m, 1F), −105.2 (m, 1F); $^1$H NMR (CDCl$_3$) δ 7.60 (m, 1H), 7.04 (m, 1H); high resolution mass spectrum, found 275.942071 (36.0%) (calcd for C$_6$H$_2$$^{37}$ClF$_7$S; 275.942447). found 273.945943 (100%) (calcd for C$_6$H$_2$$^{35}$ClF$_7$S; 273.945397). The other product, 2,6-difluorophenylsuflur pentafluoride was identified by the data obtained by Example 8 (Process II).

Example 18

Reaction of Phenylsulfur Chlorotetrafluoride and ZnF$_2$ Under a Slow Flow of an Inactive Gas (Nitrogen)

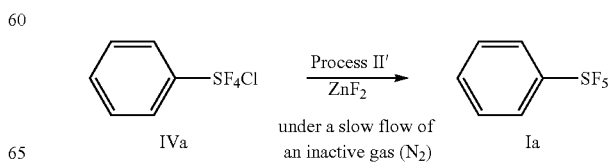

(Process II) trans-Phenylsulfur chlorotetrafluoride (trans-PhSF$_4$Cl) used for this Process was prepared in high yields by the Process I or III as shown by Examples 1, 11, 12 or 14. In a dry box, a 50 mL reaction vessel made of fluoropolymer was charged with 10.0 g (0.045 mol) of trans-PhSF$_4$Cl and 2.8 g (0.027 mol) of dry ZnF$_2$. The reaction vessel was brought out from the dry box and connected to the gas flowing system. The reaction mixture was slowly heated to 120° C. with N$_2$ flowing at the rate of 5.4 mL/minute. The reaction mixture changed from colorless to light yellow, to pink, and eventually to brown in about 30 minutes. The reaction mixture was stirred at 120° C. with N$_2$ flowing for 5 hours. After being cooled down to room temperature, the reaction mixture was checked with $^{19}$F NMR. Three major compounds (trans-PhSF$_4$Cl, cis-PhSF$_4$Cl and PhSF$_5$) were present in the reaction mixture. The ratio of trans-PhSF$_4$Cl:cis-PhSF$_4$Cl:PhSF$_5$ was 15:20:100. PhCF$_3$ (1.0 g) was added to the reaction mixture and the NMR yield of each compound was determined. The yield of trans-PhSF$_4$Cl was 2.4%, cis-PhSF$_4$Cl was 14.6%, and PhSF$_5$ was 67.2%. The reaction was not complete in 5 h at 120° C. Therefore, this experiment showed that the reaction under the flow of nitrogen was slowed down.

Example 19

Reaction of Phenylsulfur Chlorotetrafluoride and ZnF$_2$ Under a Fast Flow of Inactive Gas (Nitrogen)

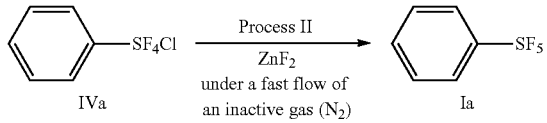

(Process II) trans-Phenylsulfur chlorotetrafluoride (trans-PhSF$_4$Cl) used for this Process was prepared in high yields by Process I or III as shown by Examples 1, 11, 12 or 14. In a dry box, a 50 mL reaction vessel made of fluoropolymer was charged with 10.0 g (0.045 mol) of trans-PhSF$_4$Cl and 2.8 g (0.027 mol) of dry ZnF$_2$. The reaction vessel was brought out from the dry box and connected to the gas flowing system. The reaction mixture was slowly heated to 120° C. with N$_2$ flowing at a rate of 26.9 mL/minute. The reaction mixture changed from colorless to light yellow, to pink, and eventually to brown in about 30 minutes. The reaction mixture was stirred at 120° C. with N$_2$ flowing for 5 hours. After being cooled down to room temperature, the reaction mixture was checked with $^{19}$F NMR. Three major compounds (trans-PhSF$_4$Cl, cis-PhSF$_4$Cl and PhSF$_5$) were present in the reaction mixture. The ratio of trans-PhSF$_4$Cl:cis-PhSF$_4$Cl:PhSF$_5$ was 22:117:100. PhCF$_3$ (2.8 g) was added to the reaction mixture and the NMR yield of each compound was determined by $^{19}$F NMR. The yield of trans-PhSF$_4$Cl was 6.7%, cis-PhSF$_4$Cl was 42.1%, and PhSF$_5$ was 38.4%. The reaction was not complete in 5 h at 120° C. and the conversion of PhSF$_4$Cl to PhSF$_5$ was lower than in Example 18. This reaction showed that the reaction under the fast flow of nitrogen was slowed down more than the reaction under the slow flow of nitrogen. In either case a flow of inactive gas has an inhibitory effect on reaction yield.

Example 20

Synthesis of Phenylsulfur Pentafluoride by Using SbF$_3$ as a Fluoride Source

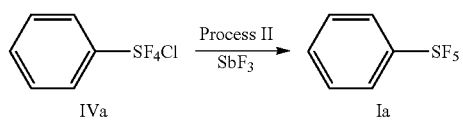

(Process II) trans-Phenylsulfur chlorotetrafluoride used for this Process was prepared in high yields by the Process I or III as shown by Examples 1, 11, 12, or 14. In a dry box, a reaction vessel made of fluoropolymer was charged with 1.0 g (4.54 mmol) of trans-phenylsulfur chlorotetrafluoride and 0.397 g (2.22 mmol) of dry SbF$_3$. The reaction vessel was brought out from the dry box and equipped with a balloon filled with N$_2$. The mixture was stirred at 80° C. for 5 h. The analysis of the reaction mixture by $^{19}$F-NMR technique showed that phenylsulfur pentafluoride was produced in 33% yield.

Example 21

Synthesis of Phenylsulfur Pentafluoride by Using a Mixture of SbF$_3$ (Fluoride Source) and SbCl$_5$ (Fluoride Source-Activating Compound) as a Fluoride Source

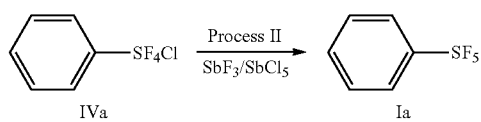

(Process II) trans-Phenylsulfur chlorotetrafluoride used for this Process was prepared in high yields by the Process I or III as shown by Examples 1, 11, 12, or 14. In a dry box, a reaction vessel made of fluoropolymer was charged with 1.0 g (4.54 mmol) of trans-phenylsulfur chlorotetrafluoride, 0.349 g (2.01 mmol) of SbF$_3$, a trace amount of SbCl$_5$, and 2 mL of dry hexane. SbCl$_5$ is a fluoride source-activating compound. SbCl$_5$ (strong Lewis acid) can complex with SbF$_3$ to form SbF$_2$(SbFCl$_5$), which can also be made by SbF$_2$Cl and SbFCl$_4$ both are fluoride sources usable in this invention. The reaction vessel was brought out from the dry box and equipped with a balloon filled with N$_2$. The mixture was stirred at room temperature for 3 days. The analysis of the reaction mixture by $^{19}$F-NMR showed that phenylsulfur pentafluoride was produced in 54% yield.

Example 22

Synthesis of Phenylsulfur Pentafluoride by Using SnF$_4$ as a Fluoride Source

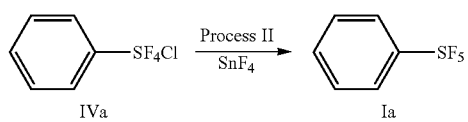

(Process II) trans-Phenylsulfur chlorotetrafluoride used for this Process was prepared in high yields by the Process I or III as shown by Examples 1, 11, 12, or 14. In a box, a reaction vessel made of fluoropolymer was charged with 1.0 g (4.54 mmol) of trans-phenylsulfur chlorotetrafluoride and 0.26 g (1.4 mmol) of dry SnF$_4$. The reaction vessel was brought out from the dry box and equipped with a balloon filled with N$_2$. The mixture was stirred at 80° C. for 2 h. The analysis of the reaction mixture by $^{19}$F-NMR showed that phenylsulfur pentafluoride was produced in 34% yield.

Example 23

Synthesis of Phenylsulfur Pentafluoride by Using TiF$_4$ as a Fluoride Source

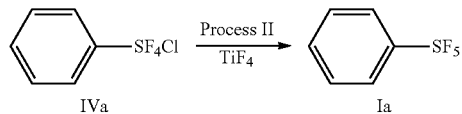

(Process II) trans-Phenylsulfur chlorotetrafluoride used for this Process was prepared in high yields by the Process I or III as shown by Examples 1, 11, 12, or 14. In a dry box, a reaction vessel made of fluoropolymer was charged with 1.0 g (4.54 mmol) of trans-phenylsulfur chlorotetrafluoride and 0.17 g (1.4 mmol) of dry TiF$_4$. The reaction vessel was brought out from the dry box and equipped with a balloon filled with N$_2$. The mixture was stirred at 80° C. for 16 h. The analysis of the reaction mixture by $^{19}$F-NMR showed that phenylsulfur pentafluoride was produced in 35% yield.

Example 24

Synthesis of Phenylsulfur Chlorotetrafluoride from Diphenyl Disulfide

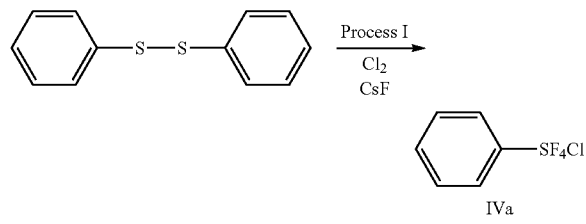

(Process I) A 500 mL round bottom flask was charged with diphenyl disulfide (21.8 g, 0.1 mol), dry CsF (243.2 g, 1.6 mol) and 200 mL of dry CH$_3$CN. The reaction mixture was cooled on an ice/water bath, and bubbled with N$_2$ (18 mL/min) for 0.5 h. After the N$_2$ flow was stopped, Cl$_2$ was bubbled into a reaction mixture at the rate of 63 mL/min for 4 h. The total amount of Cl$_2$ used was 0.68 mol. The reaction mixture was then warmed to room temperature and stirred overnight. Then, N$_2$ (18 mL/min) was bubbled through for 2 hours to remove an excess of chlorine. The reaction mixture was filtered with 100 mL of dry hexanes in a dry box. The combined filtrate was evaporated under vacuum, and the residue was distilled at reduced pressure to give a colorless liquid of phenylsulfur chlorotetrafluoride (36.3 g, 83%). The physical properties and spectral data of the product are shown in Example 1. The product was a trans isomer.

Example 25

Synthesis of P-Chlorophenylsulfur Chlorotetrafluoride from Bis(P-Chlorophenyl)disulfide

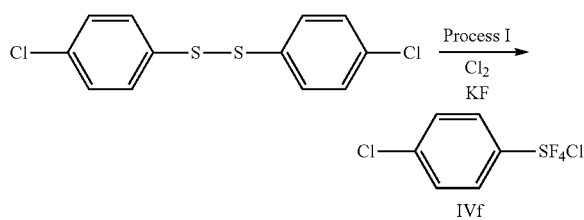

(Process I) Chlorine (Cl$_2$) was passed with a flow rate of 64 mL/min into a stirred mixture of 25.0 g (87.0 mmol) of bis(p-chlorophenyl)disulfide and 86.0 g (1.48 mol) of dry KF in 200 mL of dry acetonitrile at 5~8° C. Chlorine was passed for 3.5 h and the total amount of chlorine passed was 12.8 L (571 mmol). After that, the reaction mixture was filtered and rinsed with dry hexane. After removal of the solvent in vacuum, p-chlorophenylsulfur chlorotetrafluoride (39.5 g, 88%) as a colorless liquid was obtained; b.p. 65-66° C./2 mmHg; $^1$H NMR (CDCl$_3$) δ 7.38 (d, 2H, J=9.1 Hz), 7.65 (d, 2H, J=9.1 Hz); $^{19}$F NMR (CDCl$_3$) 137.4 (s, 4F, SF$_4$Cl). High resolution mass spectrum; found 257.927507 (13.3%) (calcd for C$_6$H$_4$F$_4$S$^{37}$Cl$_2$; 257.928790). found 255.930746 (68.9%) (calcd for C$_6$H$_4$F$_4$S$^{37}$Cl$^{35}$Cl; 255.931740). found 253.933767 (100.0%) (calcd for C$_6$H$_4$F$_4$S$^{35}$Cl$_2$; 253.934690). The NMR showed that p-chlorophenylsulfur chlorotetrafluoride obtained is a trans isomer.

Example 26

Synthesis of P-(Tert-Butyl)Phenylsulfur Chlorotetrafluoride from P-(Tert-Butyl)Benzenethiol

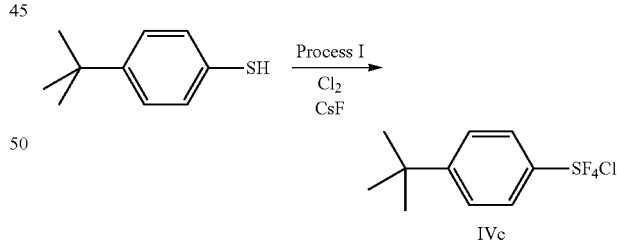

(Process I) Chlorine (Cl$_2$) was passed with a flow rate of 35 mL/min into a stirred mixture of 10.0 g (60.2 mmol) of p-(tert-butyl)benzenethiol and 91.6 g (602 mmol) of dry CsF in 150 mL of dry acetonitrile at 5~10° C. Chlorine was passed for 3.5 h and the total amount of chlorine passed was 10.1 L (452 mmol). After that, the reaction mixture was stirred at room temperature for 24 h. The reaction mixture was filtered under dry nitrogen. After removal of the solvent at reduced pressure, the residue was distilled to give 14 g (84%) of p-(tert-butyl)phenylsulfur chlorotetrafluoride; b.p. 98° C./0.3 mmHg; m.p. 93° C.; $^1$H NMR (CDCl$_3$) δ 1.32 (s, 9H, C(CH$_3$)$_3$), 7.43 (d, J=9.2 Hz, 2H, aromatic), 7.64 (d, J=9.2

Hz, 2H, aromatic); $^{19}$F NMR δ 138.3 (s, SF$_4$Cl). High resolution mass spectrum; found 278.034576 (8.8%) (calcd for C$_{10}$H$_{13}$$^{37}$ClF$_4$S; 278.033313). found 276.037526 (24.7%) (calcd for C$_{10}$H$_{13}$$^{35}$ClF$_4$S; 276.036263). Elemental analysis; Calcd for C$_{10}$H$_{13}$ClF$_4$S; C, 43.40%; H, 4.74%. Found; C, 43.69%; H, 4.74%. The NMR showed that p-(t-butyl)phenylsulfur chlorotetrafluoride was obtained as a trans isomer.

Example 27

Synthesis of Phenylsulfur Pentafluoride from Phenylsulfur Chlorotetrafluoride and ZnF$_2$

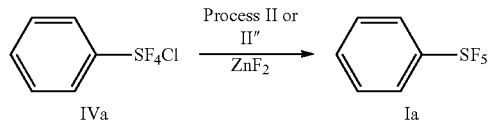

(Process II or II″) In a dry box, a reaction vessel made of fluoropolymer was charged with 1.0 g (4.54 mmol) of trans-phenylsulfur chlorotetrafluoride and 0.281 g of dry ZnF$_2$ (solid, mp 872° C., by 1500° C.). The reaction vessel was brought out from the dry box and equipped with a balloon filled with N$_2$. The mixture was heated at 80° C. for 20 h. An analysis of the reaction mixture by $^{19}$F-NMR showed that phenylsulfur pentafluoride was produced in 85% yield.

Example 28

Synthesis of Phenylsulfur Pentafluoride from Phenylsulfur Chlorotetrafluoride and ZnF$_2$

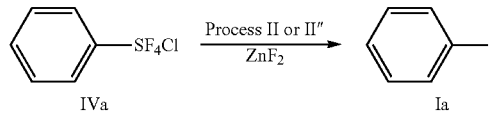

(Process II or II″) In a dry box, a reaction vessel made of fluoropolymer was charged with 1.0 g (4.54 mmol) of trans-phenylsulfur chlorotetrafluoride and 0.28 g (2.7 mmol) of dry ZnF$_2$ (solid, mp 872° C., by 1500° C.). The reaction vessel was brought out from the dry box and equipped with a balloon filled with N$_2$. The mixture was heated at 120° C. for 4 h. An analysis of the reaction mixture by $^{19}$F-NMR showed that phenylsulfur pentafluoride was produced in 88% yield.

Example 29

Synthesis of Phenylsulfur Pentafluoride from Phenylsulfur Chlorotetrafluoride and CuF$_2$

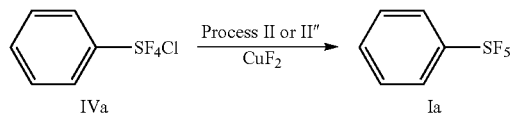

(Process II or II″) In a dry box, a reaction vessel made of fluoropolymer was charged with 1.0 g (4.54 mmol) of trans-phenylsulfur chlorotetrafluoride and 0.284 g (2.79 mmol) of dry CuF$_2$ (solid, mp ~785° C.). The reaction vessel was brought out from the dry box and equipped with a balloon filled with N$_2$. The mixture was heated at 80° C. for 22 h. An analysis of the reaction mixture by $^{19}$F-NMR showed that phenylsulfur pentafluoride was produced in 57% yield.

Example 30

Synthesis of P-Methylphenylsulfur Pentafluoride from P-Methylphenylsulfur Chlorotetrafluoride and ZnF$_2$

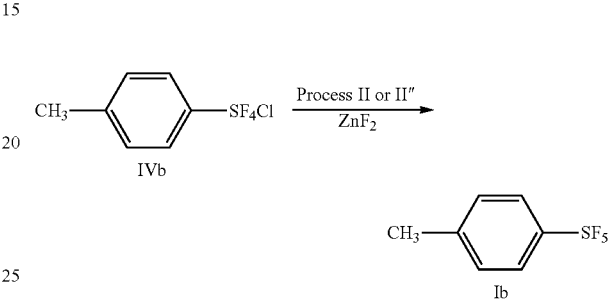

(Process II or II″) In a dry box, a reaction vessel made of fluoropolymer was charged with 1.01 g (4.26 mmol) of trans-p-methylphenylsulfur chlorotetrafluoride and 0.266 g (2.57 mmol) of dry ZnF$_2$ (solid, mp 872° C., by 1500° C.). The reaction vessel was brought out from the dry box and equipped with a balloon filled with N$_2$. The mixture was heated at 80° C. for 16 h. An analysis of the reaction mixture by $^{19}$F-NMR showed that p-methylphenylsulfur pentafluoride was produced in 79% yield.

Example 31

Synthesis of Phenylsulfur Pentafluoride from Phenylsulfur Chlorotetrafluoride and HBF$_4$ Diethyl Etherate

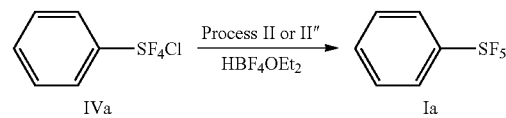

(Process II or II″) In a dry box, a reaction vessel made of fluoropolymer was charged with 1.0 g (4.5 mmol) of trans-phenylsulfur chlorotetrafluoride (trans-PhSF$_4$Cl) and 4.5 mL of dry methylene chloride. The reaction vessel was brought out from the dry box and equipped with a balloon filled with nitrogen. Into the solution, HBF$_4$ diethyl etherate (liquid) (HBF$_4$OEt$_2$) (0.88 g, 0.74 mL, 5.4 mmol) was slowly added. The reaction mixture was stirred at room temperature. The progress of the reaction was monitored by $^{19}$F NMR. After 7 hours, three major compounds (trans-PhSF$_4$Cl, cis-PhSF$_4$Cl and PhSF$_5$) were present in the reaction mixture. The ratio of trans-PhSF$_4$Cl:cis-PhSF$_4$Cl:PhSF$_5$ was 156:716:100. After 21 hours, the ratio of trans-PhSF$_4$Cl:cis-PhSF$_4$Cl:PhSF$_5$ changed to 3:6:100. An analysis of the reaction mixture by $^{19}$F-NMR showed that phenylsulfur pentafluoride (PhSF$_5$) was produced in 40% yield.

Example 32

Synthesis of Phenylsulfur Pentafluoride from Phenylsulfur Chlorotetrafluoride by Using a Mixture of ZnF$_2$ (Fluoride Source) and SbCl$_5$ Fluoride Source-Activating Compound) as a Fluoride Source

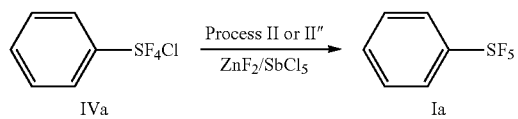

In a dry box, a reaction vessel made of fluoropolymer was charged with dry heptane (5 mL) and ZnF$_2$ (solid) (0.84, 8.2 mmol), SbCl$_5$ (liquid) (0.41 g, 0.17 mL, 1.36 mmol) was added into the mixture. To this, trans-phenylsulfur chlorotetrafluoride (trans-PhSF$_4$Cl) (3.0 g, 13.6 mmol) was slowly added. The reaction vessel was brought out from the dry box and equipped with a balloon filled with nitrogen. SbCl$_5$ is a fluoride source-activating compound. SbCl$_5$ (strong Lewis acid) can complex with ZnF$_2$ to form ZnF(SbCl$_5$), which can also be made by ZnFCl and SbFCl$_4$ both are fluoride sources usable in this invention. The reaction mixture was stirred at room temperature. The progress of the reaction was monitored by $^{19}$F NMR. After 10 minutes, the ratio of trans-PhSF$_4$Cl:cis-PhSF$_4$Cl:PhSF$_5$ was 385:0:100. After 90 minutes, the ratio of trans-PhSF$_4$Cl:cis-PhSF$_4$Cl:PhSF$_5$ changed to 63:trace:100. After 180 minutes, the ratio of trans-PhSF$_4$Cl:cis-PhSF$_4$Cl:PhSF$_5$ changed to 34:trace:100. After 17 hours, the ratio of trans-PhSF$_4$Cl:cis-PhSF$_4$Cl:PhSF$_5$ changed to 18:2:100. An analysis of the reaction mixture by $^{19}$F-NMR showed that phenylsulfur pentafluoride (PhSF$_5$) was produced in 53% yield. A small amount of the starting trans-PhSF$_4$Cl (9.4%) remained.

Example 33

Reaction of Phenylsulfur Chlorotetrafluoride and BF$_3$ Gas (Comparative Example)

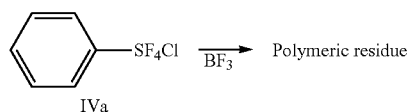

A reaction vessel made of steel was charged with 1.0 g (4.5 mmol) of trans-phenylsulfur chlorotetrafluoride and cooled on a dry ice-acetone bath. The reaction vessel was evacuated by a vacuum pump and boron trifluoride gas (BF$_3$; this boiling point is −100° C. at 1 atm) was introduced into the reaction vessel till the pressure reached 18 psi. The reaction mixture was then warmed to room temperature and stood for 3 days. During the time, the pressure was increased to 100 psi with additional BF$_3$ gas. After the reaction, it was found that all the reaction mixture became a solid residue. Phenylsulfur pentafluoride was not detected.

Example 34

Reaction of Phenylsuflur Chlorotetrafluoride and BF$_3$ Gas in Methylene Chloride (Comparative Example)

A reaction vessel made of steel was charged with 1.42 g (6.44 mmol) of trans-phenylsulfur chlorotetrafluoride and 6.4 mL of dry methylene chloride and cooled to about −100° C. by using a liquid nitrogen bath. The reaction vessel was evacuated by a vacuum pump and BF$_3$ gas (boiling point is −100° C. at 1 atm) was introduced into the reaction vessel till the pressure reached 80 psi. The reaction mixture was warmed to room temperature and stood for 5 h. During this time, the pressure was increased to 100 psi with additional BF$_3$ gas. An analysis of the reaction mixture by $^{19}$F-NMR showed that phenylsulfur pentafluoride was formed in 28% yield.

Examples 33 and 34 show that as Ou et al. reported, it was found that, when boron trifluoride (boiling point −100° C. at 1 atm) was flowed through a solution of phenylsulfur chlorotetrafluoride in a deuterium methylene chloride, phenylsulfur chlorotetrafluoride was slowly transferred to phenylsulfur pentafluoride (see Can. J. Chem., Vol. 75, pp. 1878-1884). As shown herein, however, the yield was very low or the desired product was not obtained because an undesired polymerization occurred. Examples 33 and 34 show the utility of the present invention over the conventional art production method using a fluoride gas such as boron trifluoride whose boiling point is −100° C. at 1 atm. The present invention preferably uses fluoride liquids or solids at least at 0° C. and at 1 atm, as compared to a gaseous reactant. A liquid or solid is preferable because it is easy to handle and reacts more completely than a gaseous reactant. Also, the reactant of Ou et al., although shown to react at atmospheric pressure, would require high pressure to proceed at an appreciable rate with a necessary and minimum amount of the reactant.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

I claim:
1. A process for preparing an arylsulfur pentafluoride having a formula (I):

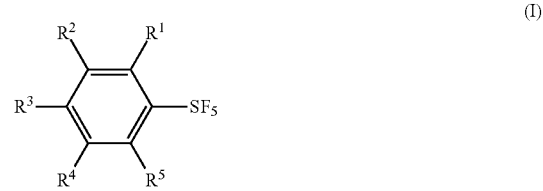

the process comprising:
reacting an arylsulfur trifluoride having a formula (V):

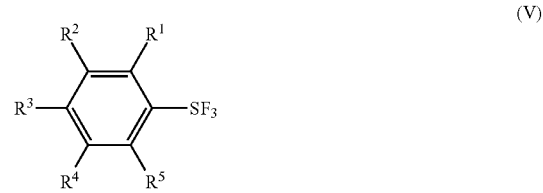

with a halogen selected from the group consisting of chlorine, bromine, iodine, and interhalogens and a fluoro salt having a formula (III) to form an arylsulfur halotetrafluoride having a formula (IV):

$$M^+F^- \quad (III)$$

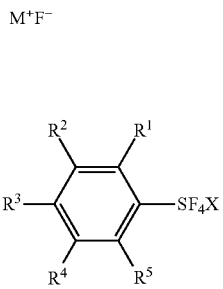
(IV)

and reacting the obtained arylsulfur halotetrafluoride with a fluoride source to form the arylsulfur pentafluoride;

in which: $R^1$, $R^2$, $R^3$, $R^4$, and $R^5$ each is independently a hydrogen atom, a halogen atom, a substituted or unsubstituted alkyl group having 1 to 18 carbon atoms, a substituted or unsubstituted aryl group having 6 to 30 carbon atoms, a nitro group, a cyano group, a substituted or unsubstituted alkanesulfonyl group having 1 to 18 carbon atoms, a substituted or unsubstituted arenesulfonyl group having 6 to 30 carbon atoms, a substituted or unsubstituted alkoxy group having 1 to 18 carbon atoms, a substituted or unsubstituted aryloxy group having 6 to 30 carbon atoms, a substituted or unsubstituted acyloxy group having from 1 to 18 carbon atoms, a substituted or unsubstituted alkanesulfonyloxy group having from 1 to 18 carbon atoms, a substituted or unsubstituted arenesulfonyloxy group having from 6 to 30 carbon atoms, a substituted or unsubstituted alkoxycarbonyl group having 2 to 18 carbon atoms, a substituted or unsubstituted aryloxycarbonyl group having 7 to 30 carbon atoms, a substituted carbamoyl group having 2 to 18 carbon atoms, a substituted amino group having 1 to 18 carbon atoms, or a $SF_5$ group;

M is a metal atom, an ammonium moiety, or a phosphonium moiety;

X is a chlorine atom, a bromine atom, or an iodine atom; and wherein the solvent is not fluorinated by said process.

2. The process of claim 1 wherein the halogen reacted with the arylsulfur trifluoride is chlorine ($Cl_2$).

3. The process of claim 1 wherein the fluoro salt having a formula (III) is an alkali metal fluoride.

4. The process of claim 1 wherein the fluoride source is at least one member selected from a group consisting of fluorides of typical elements in the Periodic Table, fluorides of transition elements in the Periodic Table, and mixture or compounds between or among these fluorides of typical elements and/or transition elements, as well as mixtures, salts, or complexes of these fluorides with organic molecules.

5. The process of claim 1, further comprising the reaction of the obtained arylsulfur halotetrafluoride with a fluoride source being performed in the presence of a halogen selected from the group of chlorine, bromine, iodine, and interhalogens to form the arylsulfur pentafluoride.

6. A process for preparing an arylsulfur halotetrafluoride having a formula (IV):

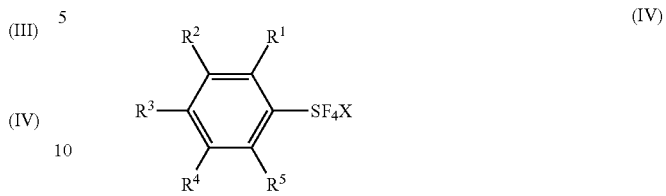

the process comprising;
reacting an arylsulfur trifluoride having a formula (V);

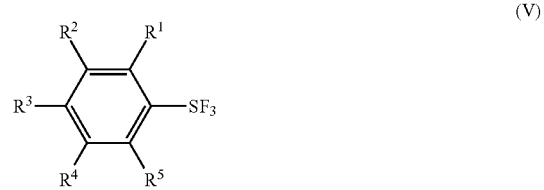

with a halogen selected from the group consisting of chlorine, bromine, iodine, and interhalogens and a fluoro salt having a formula (III) to form the arylsulfur halotetrafluoride:

$$M^+F^- \quad (III)$$

in which: $R^1$, $R^2$, $R^3$, $R^4$, and $R^5$ each is independently a hydrogen atom, a halogen atom, a substituted or unsubstituted alkyl group having 1 to 18 carbon atoms, a substituted or unsubstituted aryl group having 6 to 30 carbon atoms, a nitro group, a cyano group, a substituted or unsubstituted alkanesulfonyl group having 1 to 18 carbon atoms, a substituted or unsubstituted arenesulfonyl group having 6 to 30 carbon atoms, a substituted or unsubstituted alkoxy group having 1 to 18 carbon atoms, a substituted or unsubstituted aryloxy group having 6 to 30 carbon atoms, a substituted or unsubstituted acyloxy group having from 1 to 18 carbon atoms, a substituted or unsubstituted alkanesulfonyloxy group having from 1 to 18 carbon atoms, a substituted or unsubstituted arenesulfonyloxy group having from 6 to 30 carbon atoms, a substituted or unsubstituted alkoxycarbonyl group having 2 to 18 carbon atoms, a substituted or unsubstituted aryloxycarbonyl group having 7 to 30 carbon atoms, a substituted carbamoyl group having 2 to 18 carbon atoms, a substituted amino group having 1 to 18 carbon atoms, or a $SF_5$ group;

M is a metal atom, an ammonium moiety, or a phosphonium moiety; and

X is a chlorine atom, a bromine atom, or an iodine atom; and wherein the solvent is not fluorinated by said process.

7. The process of claim 6 wherein the halogen reacted with the arylsulfur trifluoride is chlorine ($Cl_2$).

8. The process of claim 6 wherein the fluoro salt having a formula (III) is an alkali metal fluoride.

* * * * *